US008154731B2

United States Patent
Arnvidarson et al.

(10) Patent No.: US 8,154,731 B2
(45) Date of Patent: Apr. 10, 2012

(54) METHOD AND A SYSTEM FOR THE ASSESSMENT OF SAMPLES

(75) Inventors: Börkur Arnvidarson, Reykjavik (IS); Hans Larsen, Hørsholm (DK)

(73) Assignee: Chemometec A/S, Allerod (DK)

( * ) Notice: Subject to any disclaimer, the term of this patent is extended or adjusted under 35 U.S.C. 154(b) by 544 days.

(21) Appl. No.: 11/596,141

(22) PCT Filed: May 17, 2005

(86) PCT No.: PCT/DK2005/000325
§ 371 (c)(1),
(2), (4) Date: May 27, 2008

(87) PCT Pub. No.: WO2005/111560
PCT Pub. Date: Nov. 24, 2005

(65) Prior Publication Data
US 2008/0252897 A1 Oct. 16, 2008

(30) Foreign Application Priority Data
May 14, 2004 (DK) .............................. 2004 00773

(51) Int. Cl.
*G01B 9/02* (2006.01)
*G01J 3/45* (2006.01)
*G01J 5/02* (2006.01)
(52) U.S. Cl. .................. 356/451; 250/339.07
(58) Field of Classification Search .............. 356/451; 250/339.07–339.09
See application file for complete search history.

(56) References Cited

U.S. PATENT DOCUMENTS

| 3,809,481 A * | 5/1974 | Schindler ..................... 356/452 |
| 4,088,448 A | 5/1978 | Lilja et al. |
| 5,166,749 A | 11/1992 | Curbelo et al. |
| 5,321,501 A * | 6/1994 | Swanson et al. ............. 356/479 |
| 5,379,764 A | 1/1995 | Barnes et al. |
| 5,459,317 A | 10/1995 | Small et al. |
| 5,459,677 A | 10/1995 | Kowalski et al. |
| 5,771,096 A | 6/1998 | Andersen |
| 5,933,792 A * | 8/1999 | Andersen et al. ............... 702/32 |
| 6,025,913 A * | 2/2000 | Curbelo ....................... 356/453 |
| 6,061,582 A * | 5/2000 | Small et al. .................. 600/316 |
| 6,172,752 B1 * | 1/2001 | Haruna et al. ................ 356/503 |
| 6,871,169 B1 | 3/2005 | Hazen et al. |
| 2003/0067606 A1 * | 4/2003 | Simon et al. .................. 356/450 |

(Continued)

FOREIGN PATENT DOCUMENTS
SU 1542202 5/1988
(Continued)

OTHER PUBLICATIONS

Grandmont et al. "Development of an Imaging Fourier Transform Spectrometer for Astronomy." *Proc. SPIE* vol. 4842. 2003. pp. 392-401.

(Continued)

*Primary Examiner* — Patrick J Connolly
(74) *Attorney, Agent, or Firm* — Merchant & Gould P.C.

(57) ABSTRACT

The present invention offers an alternative strategy for the correlation of interference information to chemical and/or physical properties of a sample. This strategy can be implemented in a method and a system, which offer substantial technical and commercial advantages over state of the art techniques based on interference spectroscopy. The invention further provides a method for standardizing an interferometer, as well as a method and a system using the standardized interferometer.

116 Claims, 7 Drawing Sheets

U.S. PATENT DOCUMENTS

2004/0252310 A1* 12/2004 De Lega et al. ............... 356/511

FOREIGN PATENT DOCUMENTS

WO      WO 01/67037 A1    9/2001
WO    WO 2004/109245 A2    12/2004

OTHER PUBLICATIONS

Hazen et al. "Measurement of glucose and other analytes in undiluted human serum with near-infrared transmission spectroscopy." *Analytica Chimica ACTA* vol. 371. 1998. pp. 255-267.

Jiao et al. "Adaptive imaging spectrometer in a time-domain filtering architecture." *Optics Express* 1960. vol. 11, No. 17. 2003.

Wabomba et al. "Evaluation of selectivity and robustness of near-infrared glucose measurements based on short-scan Fourier transform infrared interferograms." *Analytica Chimica ACTA*. vol. 490. 2003. pp. 325-340.

Toumi et al. "Noninvasive Blood Glucose Analysis using Near Infrared Absorption Spectroscopy." *Phase 2 Final Report. MIT Home Automation and Healthcare Consortium*. 2000.

Wabomba et al. "Design protocols for time-dependent finite impulse response digital filters based on regression analysis of Fourier transform infrared interferograms." *Chemometrics and Intelligent Laboratory Systems*. vol. 69. 2003. pp. 103-121.

Bangalore et al. "Automated detection of methanol vapour by open path Fourier transform infrared spectrometry." *Analytica Chimica ACTA*. vol. 297, Issue 3. 1994. pp. 387-403.

Martens et al. "Multivariate Calibration." *John Wiley & Sons*. 1991. pp. 90-146.

Munck et al. "Chemometrics in food science—a demonstration of the feasibility of a highly, exploratory, inductive evaluation strategy of fundamental scientific significance." *Chemometrics and Intelligent Lab. Systems*. vol. 44. 1998. pp. 31-60.

Wang et al. "Multivariate Instrument Standardization." *Anal. Chem.* vol. 63. 1991. pp. 2750-2756.

Blank et al. "Transfer of Near-Infrared Multivariat Calibrations without Standards." *Anal. Chem.* vol. 68. 1996. pp. 2987-2995.

\* cited by examiner

A

B

C

A

B

C

A

B

C

A

B

C

D

A

B

C

METHOD AND A SYSTEM FOR THE ASSESSMENT OF SAMPLES

FIELD OF THE INVENTION

The present invention relates to a method and a system for the assessment of at least one chemical and/or physical property of a sample or a specimen using spectroscopic techniques based on interferometry.

DESCRIPTION OF THE RELATED ART

Spectroscopic techniques, based on modulation have been known for several years. One of these techniques was designed by Michelson in 1891 (A. A. Michelson, *Phil. Mag.* (5), 31, 256, 1891) and generally referred to as "The Michelson Interferometer". Michelson interferometers are presently widely implemented in several commercial spectroscopic instruments for infrared measurement (ABB-Bomem Inc. USA, PerkinElmer Inc. USA, Thermo Nicolet USA, Foss Analytical Denmark). The Michelson Interferometer is based on separating a beam of light and then recombining the two beams after a path difference has occurred, thus causing interference in the detected light. Another spectroscopic method based on interferences of light is Fabry-Perot, which is based on transmitting light through two partially reflecting mirrors, and the interference occurs when the distance between the mirrors is changed. Jet other spectroscopic techniques such as Nuclear Magnetic Resonance (NMR) use similar methods of interference data, generally described by the transformation of information observed in time and/or position domain into information in frequency or wavelength domain using Fourier Transformation (e.g. transformation of "Free Induction Decay" data to shift in FT-NMR).

In order to reconstruct spectral information, the interference information (interferogram) is numerically transformed by Fourier Transformation. The spectroscopic methods based on interference techniques are therefore often call Fourier Transform spectroscopy (abbreviation FT).

Interference spectroscopy generally offers several advantages over other spectroscopic techniques, such as monochromator, prism, filters or magnetic sweeps. FT based spectrophotometers have virtually replaced those techniques in state of the art instruments. The most pronounced advantages of FT techniques are; wavelength stability, high scan speed, high spectral resolution, single detector, stable spectral response. A comprehensive description of FT-IR spectroscopy is given by P R Griffiths and J A de Haseth in "Fourier Transform Infrared Spectrometry", John Wiley & Sons, 1986 (ISBN 0-471-09902-3).

FT spectrophotometers are primarily used to record spectral information, which is used for qualitative and/or quantitative analysis of a sample. These spectroscopic analysis are methods which have been practiced for a long time and are therefore based on extensive experience, and where FT spectroscopy and personal computers have become more common they have been applied to the traditional methods. With the introduction of new techniques, new applications have been developed and also new methods, e.g. multivariate calibration, have been implemented. Thus industrial applications of spectroscopic methods have increased in number, taking advantage of the flexibility and speed of these methods.

Modern production techniques and computers have been essential in the increasing application of FT spectroscopy, since mechanical and electronical design and construction of such instruments is complicated and requires high precision and sometimes exotic materials. The computers are also necessary to perform the computationally intensive transformation from the "abstract" interference information to the "tangible" spectral information on which spectroscopists base their analysis. To take full advantage of the spectral information it is also necessary to rely on computers to apply the often-complicated multivariate calibration models needed.

Many of the inherent properties of interferometry techniques make it suitable for the standardisation of instruments. In Michelson interferometers, for instance, the wavelength is generally defined by a single laser (e.g. HeNe laser) operating at known and stable wavelength. Since it is possible to determine the properties of the laser with great accuracy, the wavelength information of the interferometer is very accurate and stable. Another aspect, the single detector, allows for a relatively simple and stable standardisation of intensity and thus the output of an FT based spectrophotometer is relatively easily standardised. By standardisation, is meant that it is possible to correlate information obtained on one instrument to information obtained on another instrument. Spectra are therefore easily transferred between locations/instrument, but equally interesting is that this allows predictive models to be developed on one instrument and then applied to results from another instrument. This feature is normally referred to as transfer of calibration. Description of methods for the standardisation of spectroscopic instrument are given by Y. Wang, D. J. Veltkamp and B. R. Kowalski ("Multivariate Instrument Standardization" *Anal. Chem.*, 63(23), pp 2750-2756, 1991) and T. B. Blank, S. T. Sum, S. D. Brown, and S. L. Monfre ("Transfer of Near-Infrared Multivariate Calibrations without Standards", *Anal. Chem,* 68(17), 2987-2995, 1996).

Transfer of calibration is obviously of interest, since reference samples with accurately known reference values for components of interest are often difficult and expensive to obtain. Thus it is possible to invest great effort in making a single calibration by obtaining accurate reference values and/or including a large number of samples, thus including variations of several interfering effects in the calibration model. This calibration can then be transferred to other instruments with little or no loss of performance. The advantage for instrument producers is obvious, since new instruments are ready to measure any feature available right away after production and when new calibrations have bee developed these can be distributed to existing instruments through exchange of information.

One general draw back of several spectrophotometric techniques, including FT spectrophotometers, is the relatively high level of mechanical complexity and physical size. These features are inherent to the present application of interferometers in spectroscopy. Demands for high spectral resolution results in large physical dimension thus defining the size of the instruments. This has generally not been a problem, since most applications for spectrophotometers are "desktop applications", usually in a laboratory. Demands from industry, for more rugged instruments, suited for installation in the hostile industrial environment are therefore not easily fulfilled.

One feature of Michelson interferometers and several other interference spectrophotometric techniques, which is a great theoretical advantage, is that information from all spectral elements is measured simultaneously, the relative weighting of each element being different in each point in the interferogram. Therefore each point of information (data point) in the interferogram contains information about all spectral elements but in combinations unique for a given data point relative to other data points in the interferogram (assuming single sided interferograms). Thus by measuring several data points it becomes possible to derive information about spectral data. The introduction of the term "data point" suggests that it is not the entire interferogram, which is measured but only discrete elements, thus in turn it becomes evident that spectral information also relates to discrete spectral data points or spectral elements, rather than continuous spectral information (e.i. all spectral elements). In short, information in a given spectral data point, obtained by interferometry, is based on weighted information from all data points of the interferogram.

Traditionally assessment of chemical or physical properties of a sample has been based on information from one, two or only few discrete wavelength(s) (e.g. absorption/transmittance or emission at a wavelength). This is partly due to the inherent simplicity of interpreting univariate correlations and partly due to the difficulty of performing complex manual calculations. With the application of multivariate calibration-methods for assessment, which has become more common with the availability of personal computers, it has been more common to perform assessment of more complicated problems, e.g. spectral interferences, overlapping spectral features, non-linearity or co-correlation.

These rather complicated assessments have become possible with the use of multivariate calibrations, e.g. MLR, PLS, PCA/PCR, ANN just to mention a few. Generally these methods are based on using information from a plurality of spectral elements to determine and/or compensate for complex co-variance or effects in the spectral information. Ideally the number of spectral data points needed is substantially greater or equal to the number of sources of variation or effects present in the measurements. Often it is advantageous to use a greater number of spectral elements and in some cases as many as 100 or even 1,000 or more spectral elements are used for the assessment of a single chemical or physical property in the presence of complex interferences. The selected number of spectral data points is highly dependent on the instrument, application and technique used to define the model.

The application of these calibration techniques in spectroscopy has its foundation in theoretical spectroscopy. For the purpose of resolving spectrally overlapping features and to take advantage of the more stable reading generally recorded at the maximum value of an absorption the spectral resolution properties of the instrument used is of great interest, and generally certain lower limits of spectral resolution are stressed for different applications. In the field of spectral resolution emphasis has been placed on the "Nyquist sampling criterion", which postulates that sampling frequency must be high enough to capture at least 2 data points per cycle of the highest frequency of interest (in the context of spectral resolution, frequency relates to the shape of a spectral feature, e.g. the width and/or steepness in the rise of absorption or emission). In spectroscopy this can be interpreted as the necessity to measure such that spectral distance between the shortest points of interest (e.g. the width, or half width of the narrowest peak or interest) is covered by at least 2 data points.

In Michelson interferometer the distance between data points in spectral frequency is dependent on the maximum difference in the distance of the two beams by the equation: $\Delta v = \Delta_{max}^{-}$, where $\Delta v$ denotes the smallest difference between two spectral data points and $\Delta_{max}$ denotes the maximum difference in the travelled distance of the two beams. In FT-IR spectroscopy the spectral information is generally represented against frequency expressed in units of 1/cm or $cm^{-1}$, this being called wavenumbers (v) but other disciplines may use different notation. In mid- and near-ir spectroscopy, where small spectral features generally have width of the order of down to about 20 $cm^{-1}$ in solid and/or liquid samples and less than 10 $cm^{-1}$ in gas samples, interferometers with maximum difference in distance of between 0.5 cm and 5 cm are common. In Michelson interferometers, where one of the mirrors is moved, this distance is twice the linear translation of the moving minor or retardation.

Another aspect of spectroscopy methods such as Fourier Transform Spectroscopy, beside spectral resolution, is the precision in the determination of ordinate information, such as attenuation or emission of electromagnetic radiation. On the bases of the discussion above concerning the spectral resolution (or more generally resolution of abscissal information), the minimum size of the collected interferogram (e.g. in relation to the movement of the moveable mirror in a Michelson interferometer) is determined. The Fourier Transformation implies that in order to improve or optimise the precision of the ordinate information for any given instrument it is necessary to improve the precision of the ordinate information in the interferogram. Beyond mechanical and/or electronical optimisation the element of measurement time offers an obvious method for such optimisation. Generally the concept of measurement time in the current context relates to taking an average of a number of individual data points, usually obtained by repeating the sweep of the interferometer for a number of times. U.S. Pat. No. 5,771,096 teaches a further optimisation of measurement time e.g. by measuring the different regions of the interferogram a different number of times, thus obtaining a relatively more precise information from the region of the interferogram at or close to the centre of the interferogram (centerburst), and combining it with an interferogram of longer retardation in order to produce spectrum with adequate spectral resolution using Fourier Transformation.

The assessment of chemical or physical properties, such as qualitative and/or quantitative analysis of chemical components, is done with the use of spectroscopic data (estimated attenuation or emission at one or more wavebands or spectral elements). Thus the above considerations concerning abscissal and ordinate information are relevant in that context, and such assessments are performed with spectral information, which fulfils these requirements.

One different approach to the use of interferometry data is proposed by Small And Arnold (U.S. Pat. No. 549,317 and U.S. Pat. No. 6,061,582), where a section of the interferogram, not including the centerburst, is used to extract spectral feature, small in bandwidth compared to the background signal. The effect of the method is equivalent to high-pass filtration.

In some state of the art methods for assessment based on spectral information substantially all available spectral data points are included while in others only a limited number of spectral data points are used. The fact that each data point in an interferogram represent information about all spectral elements and each spectral element, constructed from the interferogram, contains weighted information from each data point of the interferogram (property of the Fourier transformation), implies that regardless of whether only relatively few or substantially all available spectral elements are used then weighted information from all interferogram data points are included.

In theory quality of information, such as spectral information constructed on the bases of interferogram, improves by increasing the number observations (e.i. data points), in analogy to the general property of the variance of the mean. Assuming that information in an interferogram data point is pure information about spectral elements and to some extent random error, it can be assumed that information quality of spectral data points constructed on the bases of interferogram data points improves by including more data points as does spectral information (e.i. resolution). In the present context "information quality" refers to properties such as accuracy and/or precision, generally associated with intensities, with relevance to the performance of an assessment. On the other hand, the observed interferogram can be influenced by other sources of information beside spectral information, such as temperature, time dependent electrical noise to mention a few, and under these conditions the inclusion of all information can have destructive information on the quality of the assessment.

In the application of present state-of-the-art interferometry due consideration has been given to the factors potentially limiting the performance of the instruments and models used for assessment. The mechanical and electronical components used have improved significantly during the past decades and the performance of instruments has benefited from that.

One technological field which has been used in many state of the art spectrophotometers is the field of piezo electric actuators. These have found application in instruments offering dynamic alignment of optical components (Varian Inc, USA), due to the fast and precise movement, which can be brought about with piezo electric actuators over short distance (normally about 1 µm). Further piezo electric actuators have been used in visible image spectroscopy (Yang Jiao, et. al., *Optics Express*, 11, 1961-1965, 2003), and in high resolution astronomy imaging step-scan interferometer (Frédéric Grandmont, Laurent Drissen and Gilles Joncas, *Proc. SPIE*, 4842, 392-401, 2003).

SUMMARY OF THE INVENTION

The present invention offers an alternative strategy for the correlation of interference information to chemical and/or physical properties of a sample. This strategy can be implemented in a method and a system, which offer substantial technical and commercial advantages over state of the art techniques based on interference spectroscopy.

It was found that it is possible to perform assessment of chemical and/or physical properties of a sample or sample material with substantial simplification of methods and systems currently used according to the state of the art in the field, furthermore without substantial reduction in the statistical quality of the assessment compared to assessments conducted according to state of the art methods using state of the art systems. Indeed several embodiments of the present invention offer substantial advantage compared to the current methods, and several preferred embodiments of the present invention make it feasible to perform assessments hitherto not feasible using the methods and system of the state of the art in the field.

The present invention demonstrates that information in only a few data points from an interferogram, or other interference information can be adequate to perform an assessment with performance that is comparable in performance to an assessment according to the state of the art methods and systems. Spectral information constructed on the bases of the reduced number of data points in the interferogram, e.g. by Fourier Transformation, turns out to be severely distorted in several embodiments but surprisingly this information was found well suited to perform assessment of acceptable statistical quality.

It has been found, that methods and systems based on the current application offer substantial advantage compared to the state of the art methods and systems, thus having commercial potential in the application of such methods and/or systems.

One aspect of the invention relates to a method and a system for assessing at least one chemical or physical property of a sample, wherein the assessment is based on interferometri or information derived therefrom. The method and system according to the invention allows for a simplified and robust measurement. Accordingly, in one embodiment the invention relates to a method for the assessment of at least one chemical or physical property of a sample comprising establishing modulation means, said modulation means comprising an interferometer, wherein an optical path difference is obtained through the movement of at least one optical component in said interferometer using a solid-state actuator, interferometer modulating light emitted from the sample, having interacted with the sample and/or being emitted to the sample, detecting modulated light in the NIR and/or the IR spectral region or a property derived from said modulated light on at least one detector, correlating the obtained information to the at least one chemical or physical property.

Correspondingly, the invention relates to a system for the assessment of at least one chemical or physical property of a sample comprising modulation means, said modulation means comprising an interferometer, wherein an optical path difference is obtained through the movement of at least one optical component in said interferometer using a solid-state actuator, said interferometer being capable of modulating light emitted from the sample, having interacted with the sample and/or being emitted to the sample, at least one detector capable of detecting modulated light in the NIR and/or the IR spectral region or a property derived from said modulated light, means for correlating the obtained information to the at least one chemical or physical property.

In another embodiment the invention relates to a method and a system for the assessment of at least one chemical or physical property of a sample comprising establishing modulation means, said modulation means comprising an interferometer, wherein an optical path difference is obtained through the movement of at least one optical component in said interferometer, said optical component having a scan length capable of forming a maximum optical path difference of between 10 µm to 10,000 µm, such as of between 10 and 2,000 µm, interferometer modulating light emitted from the sample, having interacted with the sample and/or being emitted to the sample, detecting modulated light having a wavelength of at least 1,000 nm or a property derived from said modulated light on at least one detector, correlating the obtained information to the at least one chemical or physical property.

The present invention is especially suitable for designing a method and a system capable of obtaining an interferogram or information derived therefrom without using external reference or an external signal when information about modulated light signals is acquired. Accordingly, in yet another embodiment the invention relates to a method for the assessment of at least one chemical or physical property of a sample comprising establishing modulation means, said modulation means comprising an interferometer, wherein an optical path difference is obtained through the movement of at least one optical component in said interferometer, interferometer modulating light emitted from the sample, having interacted with the sample and/or being emitted to the sample, detecting modulated light or a property derived from said modulated light on at least one detector, wherein acquisition of information about the modulated light signal is made without reference to external information or external signal, correlating information about the detected light to an optical path length obtaining an interferogram, correlating the obtained interferogram, and/or the information about the detected light and the optical path length to the at least one chemical or physical property.

Furthermore, the invention relates to a system for the assessment of at least one chemical or physical property of a sample comprising modulation means, said modulation means comprising an interferometer, wherein an optical path difference is obtained through the movement of at least one optical component in said interferometer, said interferometer being capable of modulating light emitted from the sample, having interacted with the sample and/or being emitted to the sample, at least one detector capable of detecting modulated light or a property derived from said modulated light, wherein acquisition of information about the modulated light signal is made without reference to external information or external signal, means for correlating information about the detected light to an optical path length obtaining an interferogram, and means for correlating the obtained interferogram, and/or the information about the detected light and the optical path length to the at least one chemical or physical property.

The present invention furthermore allows for a simplified method of assessing a chemical or physical property of a sample by determining or estimating interference loadings for a single spectral element. Accordingly, in one aspect the invention relates to a method for the assessment of at least one chemical or physical property of a sample comprising a) obtaining an interferogram representing detected modulation of light having interacted with the sample, where the information in the interferogram can be correlated to optical path difference, b) determining or estimating interference loadings for a single spectral element or a single spectral feature corresponding to the said correlation to optical path difference and under conditions substantially similar to conditions forming the interferogram, c) optionally repeating step b) a predetermined number of times, d) determining scores of interference loadings in said interferogram, and e) correlating said scores to the at least one chemical or physical property.

Correspondingly, the invention relates to a system for the assessment of at least one chemical or physical property of a sample comprising a) means for obtaining an interferogram representing detected modulation of light having interacted with the sample, where the information in the interferogram can be correlated to optical path difference, b) at least one detector for determining or estimating interference loadings for a single spectral element or a single spectral feature corresponding to the said correlation to optical path difference and under conditions substantially similar to conditions forming the interferogram, c) means for optionally repeating step b) a predetermined number of times, d) means for determining scores of interference loadings in said interferogram, and e) means for correlating said scores to the at least one chemical or physical property.

The present invention also provides a simplified method for standardizing an apparatus for assessing a chemical or physical property of a sample. Accordingly, the invention relates to a method for standardizing an interferometer, said method comprising a. generating at least one interferogram from at least one standardization sample in said interferometer, b. providing a standard interferogram for said standard sample or for at least one standard feature, c. correlating said standard interferogram to said at least one interferogram obtained in step a), and d. standardizing the interferometer based on correlation information obtained in step c).

Furthermore, the invention relates to a method and a system standardized according to the invention. Thus, the invention relates to a method for the assessment of at least one chemical or physical property of a sample comprising establishing an interferometer standardized as defined above, obtaining at least one interferogram from the sample, standardizing the interferogram based on standardisation parameters obtained from standardization of the interferometer, and correlating the standardized interferogram or information derived from said interferogram to the at least one chemical or physical property of the sample.

Correspondingly, the invention relates to a system for the assessment of at least one chemical or physical property of a sample comprising an interferometer standardized as defined above, means for obtaining at least one interferogram from the sample, means for standardizing the interferogram based on standardisation parameters obtained from standardization of the interferometer, and means for correlating the standardized interferogram or information derived from said interferogram to the at least one chemical or physical property of the sample.

The objective of a uni- or multivariate method for the assessment of a property (e.g. chemical and/or physical property) based on spectroscopic data is to construct a model, which can derive the information of interest from the spectral information (e.g. a calibration model). In the case of a univariate system (e.g. a system and/or sample where a signal responsive to the property of interest is obtainable, being free of any interference) it is generally sufficient to use a single spectral information, while the more general multivariate methods require information from multiple spectral elements and/or spectral features.

When creating models for the assessment of chemical and/or physical properties it is greatly desirable and normally necessary to have access to information which reflects a number of independent sources of variations, which preferably correlate to the property in question and/or any other property affecting the property in question. Generally, if considering a system with n independent properties, it is necessary to have access to at least n sources of information and generally more than n, depending on to which degree the sources of information reflect independent variations and/or random variations (e.g. noise). When considering spectroscopy one thus generally seeks out a number of suitable spectral elements or wavebands that reflect such independent variations.

One preferred method of the current invention for optimisation of the use of interference information for the assessment of a chemical or physical property, preferably from a plurality of measurement of plurality of samples with known properties, is firstly preferably to construct spectral information from the interference information (e.g. emission or extinction/absorbance) and then applying multivariate calibration methods to the spectral information, where the result of these methods is used to assign importance or validity to the different spectral elements. Secondly to use the importance or validity information to identify spectral elements or spectral features, which represent information correlating to the property being assessed. Thirdly determining preferred correlation between the identified spectral elements or spectral features and the interference data, preferably taking into consideration one or more factors such as repeated measurement, repeated standardisation of interference system, different interference systems, different sample condition, or in general any factor which could influence the determination of interference information. Fourthly using the preferred correlation to estimate spectral properties of the sample, preferably repeating the steps above using same or different sample or measurement of samples to finally arrive at a model suitable for the assessment of a chemical or physical parameter. Generally a model generated in accordance with such procedure is characterised by inherent stability with respect to condition of sample or instrument used. One preferred property of such model is that not the entire interference information is used for the assessment, but only parts or regions which exhibit favourable properties. Other equally preferred embodiments of the present invention are based on the direct inclusion of interference information in a model, without any conversion to spectral information, and may preferred embodiments include both spectral information and interference information.

Any electromagnetic spectrum consists of infinite number of spectral elements. The number of components in a spectrum is therefore unlimited but to the extent that a spectral feature, e.g. attenuation and/or emission of electromagnetic radiation, can be considered to be finite in resolution such information can be represented by a collection of a suitable number of spectral elements, where the suitable number of spectral elements preferably allows substantially correct reproduction of the spectral feature through interpolation.

According to the state of the art methods for assessment based on spectroscopy the requirements to resolution relating to the representation of spectral features encountered, are generally adapted. Contrary to this, it has surprisingly been found, that using conditions for interferometry based spectroscopy, which reduce the resolution of the representation of spectral features (when subjected to the methods of the state of the art spectroscopic techniques such as Fourier Transformation), results with a satisfactory statistical quality of several assessments of chemical and/or physical properties is obtained. Several of the most preferred embodiments of the present invention allow an assessment to be made under conditions, which in traditional application of interference/FT spectroscopy renders severely distorted spectral information.

In relation to the application of interferometry based spectroscopy, such as the Fourier Transform Spectroscopy, it has been found that for instance the distance in the movement of the movable mirror of the Michelson interferometer, necessary for satisfactory assessment according to the present invention, is substantially less than the distance needed to produce spectral representation of the system being investigated with the general requirement to spectral resolution. Furthermore it has been found that in many preferred embodiments of the present invention satisfactory results can be obtained by selectively using information from only a part or parts of the collected interference information.

Generally the interference data can be viewed as a sum of simple functions or waveforms. For the Michelson Interferometer the intensity of the interferogram can be expressed as $$I(\delta) = \int_{-\infty}^{+\infty} B(v) \cos(2\pi\delta) dv$$

where $I(\delta)$ is the intensity at the retardation $\delta$ (relating to the path difference between the two beams), and $B(v)$ is the intensity of the signal at the spectral element or wave number $v$ (e.g. a spectrum), as viewed by the detector (e.g. spectrum modified by the spectral response of the various optical components).

Thus the observed interferogram can be viewed as a sum of cosine functions of the retardation, the retardation defined as being zero at the position where the distance between the two mirrors is equal (e.g. at centerburst). Thus each spectral component (e.g. single frequency) contributes to the interferogram as a cosine function and in determining $B(v)$, the Fourier Transformation gives an estimate of the intensity of the corresponding cosine function in the interferogram. It is therefore simple to arrive at the conclusion, that the number of spectral components which can be derived from an interferogram is in some way related to the number of collected interferogram elements, e.g. in relation to the need to have a certain number of known entries when trying to solve a number of unknowns in an equation.

When it surprisingly has been found that methods and systems according to the present invention nevertheless show comparable and often superior performance in the assessment of chemical and/or physical property, although a substantially fewer interferometer elements are used and/or substantially less range of an interferogram is used (corresponding to the maximum movement of the mirror assuming Michelson interferometer or the like) it is in many cases related to the relatively high degree of co-linearity among the different spectral elements.

Any two different cosine functions representing different spectral element are "orthogonal" to each other, as defined in the discipline of numerical analysis, assuming sufficient range of $\delta$(ideally infinitesimal). Also it follows, that two different combinations of orthogonal functions (e.g. linear combinations) are orthogonal. The "score" of wave function, such as a cosine function, on interference data is a measure of the contribution of that function in the measured data. This score relates therefore to the intensity of such a function, and if it is a single cosine function it correlates to the emittance or transmittance of corresponding spectral wavelength, or if it is a combination of wave functions, e.g. representation of spectral feature, it corresponds to the property relating to such combination, in similar manner as amount of a compound corresponds to emission or absorption of energy.

When considering typical assessment of a chemical and/or physical component it would typically be performed under conditions spanning a defined and/or finite range of variations, e.g. spectral variations, usually such range of variation would be included in the development of the multivariate model. Under such conditions, the weighting of any two spectral elements found close to each other, will be closely correlated (for instance the attenuation or emission at frequency $v$ and $v+\Delta$, where $\Delta$ is small compared to the width of the attenuation or emission spectral feature). Therefore the intensities of wave functions at frequencies $v$ and $v+\Delta$ can be regarded as being highly correlated. In the development of a multivariate model under such conditions, it is obvious to a person skilled in the art, that the task becomes the one of identifying underlying structures in the interferogram which correlate to the parameter of interest, rather than isolating individual spectral elements, such structures could for instance be the effect of the part or the entire attenuation or emission spectral feature (e.g. an absorption band).

The rank of a data set is defined as the number of orthogonal vectors (e.g. eigenvectors) that are needed to span or represent "sensible" data. Ideally any dimensionality in the data set such as a number of spectra of samples of varying composition, beyond the rank represents noise or random behaviour. For instance if we consider a spectral system consisting of only four spectral elements that can appear at any intensity irrespective of the intensities of the other spectral elements, then the rank of a collection of interferograms collected from this spectral system will have the rank four regardless of the number of measured samples (greater than 4). Ideally, regardless of how many data points there are collected the interferogram can be decomposed into the four fundamental sets of cosine functions, each set of cosine functions being a weighted linear combination of one or more cosine functions. If there were additional spectral elements in the system, but these spectral elements were correlated to any of the four initial elements, e.g. when one of the initial spectral elements changed in intensity, this would imply a given change in the intensity of the additional spectral elements, then the rank of the system would still be only four, since interferogram would of course be different, but it would still be only constructed of four separate sources of variation. Ideally deviation between the observations and the combination of the existing wave functions can be considered to be random noise. If the "residual" information is not only random noise, but consists also of some systematic variations, then the rank of the data set is larger than four.

In many preferred embodiments of the present invention the size of the interferogram data (e.g. number of data points) is substantially of the same size as the rank of the spectral system.

In Fourier Transform Spectroscopy, e.g. when applied to data collected from a Michelson interferometer, the resolution of the interferogram or the distance in the position of the movable mirror(s) between two measurements defines the frequency region of the derived spectrum, the shorter the distance between adjacent points in the interferogram the higher the maximum spectral frequency is represented in the derived spectrum. Thus virtually no improvement is observed in the derived spectrum when the distance between measurements is decreased beyond the necessary limit defined by the spectral range of interest. Since many embodiment of the present invention can be viewed as the extraction of latent structures, rather than wave function information, from the collected interferogram, then there is often observed a significant improvement in assessment of a chemical and/or a physical property by increasing the resolution of the collected interferogram. In particular this allows for the optimisation of the effort of sampling, since both sampling of data and movement can generally be conducted under optimal conditions, often without substantial consideration to the other.

The quality of the collected interference information is often dependent on the quality of the determination of the amplitude information. Generally the amplitude information is obtained by digitising an electrical signal representing or correlating to the detected signal, e.g. by using an analogue to digital converter (ADC). Since the preferred determination of amplitude information reflects all significant amplitude information it implies that a certain resolution must be applied in the ADC. In order to represent the interference information with adequate resolution, it is generally preferred to amplify the electrical signal using variable amplification (e.g. gain-ranging). Another preferred embodiment is to use more than one ADC, preferably where the signal measured by each ADC has been amplified differently. One preferred embodiment of such a configuration uses the digitised result from a low amplification to construct a difference signal, which in turn is further amplified and digitised, and where the interference information is constructed using the combination of the signal with low amplification and the difference signal with higher amplification. Many of these embodiments are preferred when the resolution of the ADC used is relatively low, e.g. 8, 12, 16 or 20 bits.

In the collection of interference data, a substantial accuracy as well as precision is required in the retardation, in order to obtain accurate spectral information. For that purpose the interferometers are generally equipped with a signal generation of accurately know properties, such as a laser, and to use the modulation of this signal to accurately determine the retardation The modulated signal of a monochromatic source, such as a laser, generates a single wave function when modulated with a Michelson interferometer. By monitoring this signal, it is possible to determine accurately and precisely the retardations and this in turn is used to control the collection of data. Similar methods are used in several embodiments of the present invention, but preferably sources not strictly monochromatic, such as laser diodes or more preferably light emitting diodes are used.

In some preferred embodiments even no such additional signal generator is used. In several of these embodiments the precision of the collected interference data is assured through reproducible generation of interference, e.g. the movement of a mirror in a Michelson interferometer, while in others, the form of the collected interference data of the sample or system is used to assure reproducible collection of interference data, preferably in embodiments where physical and/or chemical conditions of the system being assessed are considerably stable. Also several preferred embodiments of the present invention use a predefined and/or and adaptive transformation and/or standardisation of collected data in order to produce an interferogram representing a precise and accurate retardation.

From the above it is apparent that according to the present state of the art methods of interference spectroscopy, such as Fourier Transform spectroscopy, the determination of spectral information based on interference information which is under-determined with respect to the ability to resolve spectral elements (e.g. short movement of a mirror in a Michelson interferometer) suffers severely, to a degree where the spectral information is virtually distorted. Nevertheless it has surprisingly been found, that according to many preferred methods of the present invention, that it is possible to fully or partly construct the spectral information, preferably using methods that are based on the extraction of latent variables (e.g. loadings in PCA or PLS) from a vector(s) of data, such as an interferogram or even only parts of interferograms.

One simple, and often preferred method of the current invention is to extract cosine wave functions directly from an interferogram, preferably where the interferogram is collected with high resolution, while in other methods a wave function of a more complex nature is used, preferably such wave functions are substantially orthogonal to each other, for instance when the complex wave function are a combination, often linear combination of cosine functions. The method allows the estimation of the intensity of any wave function (e.g. scores in PCA or PLS), in principle without any limitation relating to the resolution and/or size of the interferogram. The deviation from ideal orthogonally using such methods, in particular when deriving single cosine functions, is generally visible as oscillating "noise" of stable or variable frequency but these can be easily removed or suppressed using numerical methods such as filtration or apodization.

The method of correlating scores of wave functions, e.g. cosine functions, to spectral property is used in many preferred embodiments, including where substantially the entire spectral range of the observed interference is estimated, but preferably where only one or more parts of the spectral range are estimated, preferably using variable spectral resolution, when the resolution is determined on the bases of local coherence of the spectral information, e.g. where the frequency of the different wave function is determined by the property of the spectral system under investigation rather than being substantially equally distributed.

Many preferred methods of the present invention use a method where the "true" spectral features of the sample, are represented by one or more latent variables (e.g. loadings) and by constructing scores for the spectral loadings, based on scores obtained by interference loading it allows a substantially correct reconstruction of the spectral features as a whole, rather than the individual spectral frequencies. Furthermore, these methods can successfully be applied to an interferogram collected using maximum retardation similar to those commonly used under state of the art conditions, to even further enhance the apparent representation of spectral elements, beyond what is possible through Fourier Transformation.

It has been demonstrated that the performance of a prediction model, when used with data from different instruments, or instruments operating under different conditions, is generally improved upon standardisation (Wang et al.). This allows a predictive model to be developed on one instrument under given conditions and subsequently applied on data from another instrument or data obtained under different conditions. The method of standardisation has generally the purpose of removing, correcting or suppressing differences in ordinate and/or abscissal spectral representation from one instrument/condition to another.

The standardisation of instruments is performed on the spectral output of instrument (see U.S. Pat. Nos. 5,459,677 and 5,933,792), allowing the shifting of wavelength or frequency information and/or the adjustment of intensity. Several preferred methods of the present invention use methods of standardisation as a transformation of interference data, preferably by measuring samples and/or systems of predetermined and/or known conditions, or more preferably by relating to a predetermined and/or observed properties of the collected interference data. Any spectral information derived from such a standardised interferogram will reflect "true" or standardised spectral data.

The standardisation of the retardation or optical path difference will ensure stability of the spectral frequency, while the spectral intensity might need further treatment. It is therefore preferred to perform the standardisation in two steps, one step focusing on frequency and another focusing on intensity. Both steps can be carried out in either interferogram data or spectral data, but generally it is preferred to do the frequency standardisation on interferogram data and intensity standardisation on spectral data.

Many features of the present invention are methods and systems which offer substantial advantage compared to state of the art method of similar assessments. Generally such advantage is simplified mechanical construction (e.g. shorter movements of optical elements, reduced demands to the quality of mechanical parts, smaller dimension of an interference module, simpler standardisation of modules/instruments), improved sensitivity (e.g. larger numerical aperture, less degree of spectral separation of filters), simplification of calculations means (e.g. less computing power, less demand for computer memory), more reliable models for assessment (e.g. more simple transfer of model between modules/instruments).

One preferred method for the construction of an interferometer according to the present invention is the use of "solid interferometers", were the term solid in the current context means construction where the different components of the interferometer are in rigid configuration with respect to each other, preferably where "rigid" is defined as large resistance to movement in the frequency range of the moving of any part of the interferometer. One preferred construction of a solid interferometer is one, where movement of a part of the interferometer is performed with the use of one or several piezo, thermal or electrostatic actuator(s). One preferred embodiment is one, where one or more of the optical components are an integrated part of an integrated circuit (IC) or modules produced using the method of micromachining (MEMS).

Preferred embodiments of the current invention concern a Michelson interferometer, where both mirrors are moved substantially simultaneously and thus obtaining double retardation or optical path difference compared to a single moving mirror. This is in particularly a preferred embodiment, when the movement of the mirrors is brought about by "rigid" or solid-state actuators, such as piezo, thermal or electrostatic, actuators, preferably when the same driving/controlling system is applied to more than one actuator. In case individual actuator elements displace substantial deviation from parallel motion, two such actuator elements, showing similar, or preferably substantially identical deviation, are paired in a manner where the deviations from parallel motion of the two actuator elements substantially eliminate each other.

These properties offer obvious advantages to an instrument producer, allowing the construction of more simple instruments for assessment based on spectral interference such as interferometers. Also the advantage to the user of instruments based on the present invention is obvious due to improved applicability (e.g. mechanical stability) of such instruments with little or no loss of performance, compared to the state of the art instruments.

DESCRIPTION OF THE INVENTION

Figure 1:
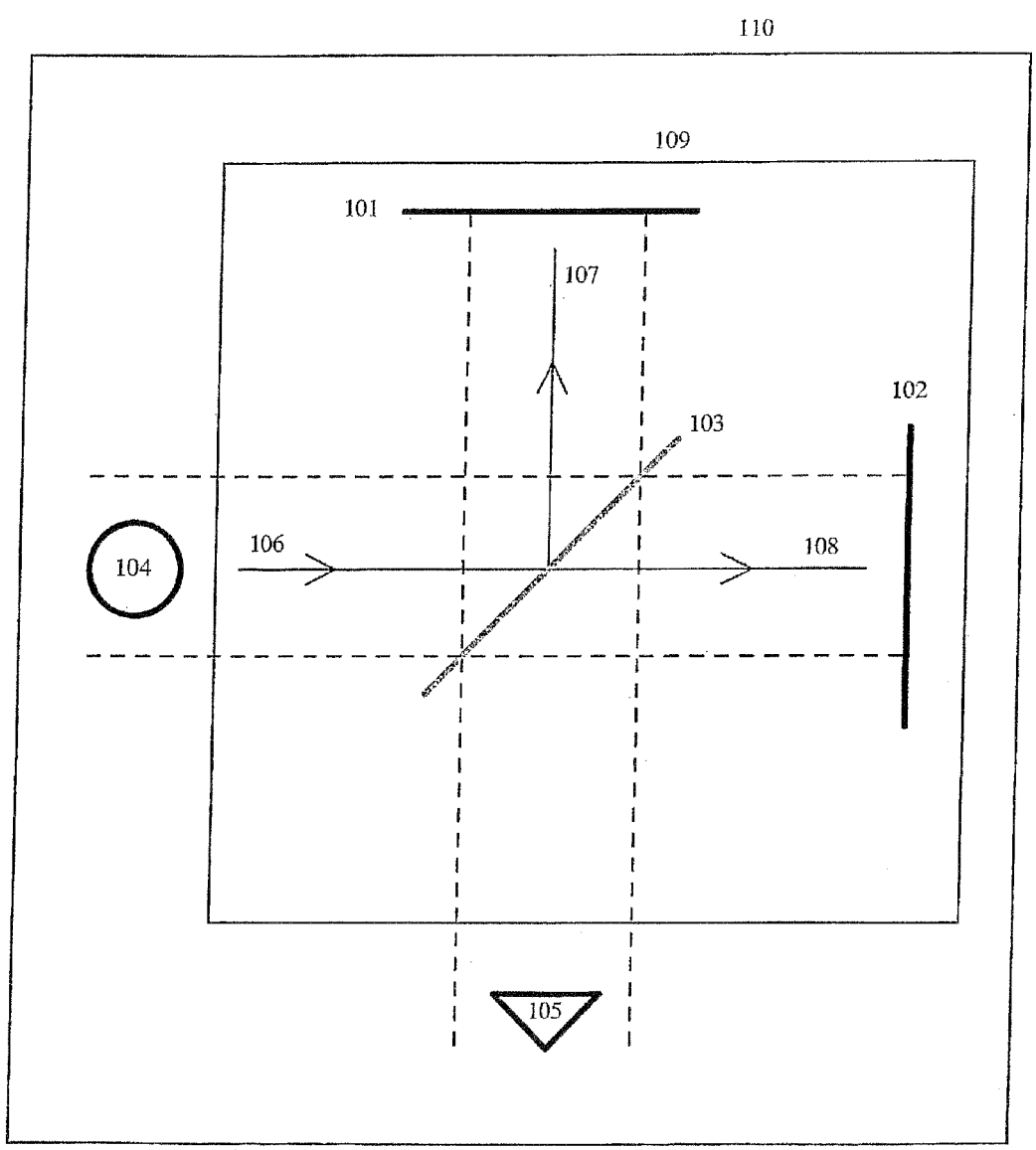
FIG. 1 illustrates the principles of Michelson interferometer.

Preferred methods of the current invention relate to assessment of chemical and/or a physical property of a sample, based on various spectral regions. Further in the different spectral region, the spectral resolution, defined by the maximum optical path, is preferably limited as for instance in the far-IR region to be less than 4 $cm^{-1}$, preferably less than 8 cm$^{-1}$, more preferably less than 16 cm$^{-1}$, more preferably less than 32 cm$^{-1}$, more preferably less than 64 cm$^{-1}$, more preferably less than 96 cm$^{-1}$, more preferably less than 128 cm$^{-1}$, more preferably less than 160 cm$^{-1}$, more preferably less than 192 cm$^{-1}$, more preferably less than 224 cm$^{-1}$, more preferably less than 256 cm$^{-1}$.

Similarly, when considering the mid-IR and near-IR spectral region the resolution is usually less than 8 cm$^{-1}$, preferably less than 16 cm$^{-1}$, more preferably less than 32 cm$^{-1}$, more preferably less than 64 cm$^{-1}$, more preferably less than 96 cm$^{-1}$, more preferably less than 128 cm$^{-1}$, more preferably less than 160 cm$^{-1}$, more preferably less than 192 cm$^{-1}$, more preferably less than 224 cm$^{-1}$, more preferably less than 256 cm$^{-1}$.

When considering visible and UV spectral regions a preferred resolution according to embodiments of the current invention is less than 16 cm$^{-1}$, preferably less than 32 cm$^{-1}$, more preferably less than 64 cm$^{-1}$, more preferably less than 96 cm$^{-1}$, more preferably less than 128 cm$^{-1}$, more preferably less than 160 cm$^{-1}$, more preferably less than 192 cm$^{-1}$, more preferably less than 224 cm$^{-1}$, more preferably less than 256 cm$^{-1}$.

When performing assessment of chemical and/or physical properties of a sample, many preferred embodiments involve the use of at least one light source. Depending on the spectral region used for the assessment, it is preferred that the at least one light source is a light source which emits light in the mid-IR region, near-IR region, visible region, UV region, preferably where the light source is a thermal emitting light source, light emitting diode or laser diode, preferably comprising more than one light source of similar or different properties, preferably where light sources with similar properties can enable more intense illumination and where light sources with different properties can extend the spectral range of an embodiment of the current invention.

Generally, when considering embodiments in the near- and min-IR spectral region it is preferred that light emitted onto, through or from a sample or specimen is of wavelength longer than 1,000 nm, preferably longer than 1,500 nm, more preferably longer than 2,000 nm, more preferably longer than 2,500 nm. Using frequency rather than wavelength to define preferred spectral region many embodiments employ light emitted onto, through or from a sample or specimen of frequency between 10,000 and 800 cm$^{-1}$, preferably between 5,000 and 900 cm$^{-1}$, more preferably between 3,000 and 1,000 cm$^{-1}$, more preferably between 2,000 and 1,000 cm$^{-1}$, similarly often preferred spectral region is of frequency between 10,000 and 2,000 cm$^{-1}$, preferably between 5,000 and 2,000 cm$^{-1}$, more preferably between 3,000 and 2,000 cm$^{-1}$.

A much preferred modulating means are means where spectral information is modulated in such a way that frequency or wavelength intensities are substantially represented in time or distance domain, preferably where the modulation is by the means of an interferometer, such as "Michelson Interferometer" or "Fabry-Perot Interferometer". Preferred relative arrangement of the sample relative to, or within such preferred modulation means is where a sample is placed between a light source and the modulation means, preferably where the sample is placed between the modulating means and the detector. When the modulation means is a "Michelson Interferometer" it is preferred to the sample is placed between the beam splitter and one of the mirrors in some embodiments of the present invention.

One often preferred feature of the current invention is the possibility of implementing a large collection angle, and thus preferably increasing the amount of light transmitted into, through or out of the modulation means. In particular it is preferred that the collection angle of an modulation means is more than 5 degrees, preferably more than 10 degrees, preferably more than 15 degrees, preferably more than 20 degrees, preferably more than 30 degrees, preferably more than 45 degrees.

Another feature, offering similar enhancement of embodiments of the current invention are a large divergence angle through the modulating means, e.g. an interferometer, preferably using the short maximum optical path difference often preferred, for instance due to limited self apodization. Preferred angles of optical divergence of a modulation mean is more than 2 degrees, preferably more than 4 degrees, preferably more than 6 degrees, preferably more than 8 degrees, preferably more than 10 degrees, preferably more than 15 degrees.

One particularly preferred embodiment of the current invention is one where the size of the interferometer is small, e.g. defined by one of the physical dimensions of the interferometer, preferably the largest physical dimension of the interferometer, since the size of the interferometer can define the applicability of many methods. Preferably physical dimensions of an interferometer according to the present invention are less than 30 cm, preferably less than 20 cm, more preferably less than 15 cm, more preferably less than 10 cm, more preferably less than 8 cm, more preferably less than 6 cm, more preferably less than 4 cm, more preferably less than 3 cm, more preferably less than 2 cm, more preferably less than 1 cm.

A typical interferometer, e.g. a Michelson interferometer, contains a mirror which can be moved, and thus changing the optical path difference of the interferometer. Many embodiments of the current invention have such a movable mirror, where it is preferred to reduce the movement of the mirror, in order to allow the suitable mechanical construction. In such often preferred embodiment the scan length of a mirror in the interferometer is less than 1,000 μm, preferably less than 750 μm, more preferably less than 500 μm, more preferably less than 300 μm, more preferably less than 200 μm, more preferably less than 100 μm, more preferably less than 75 μm, more preferably less than 50 μm, more preferably less than 30 μm, more preferably less than 20 μm, more preferably less than 10 μm. Generally, the movement of an optical component of the modulation means defines the optical path difference of an interferometer, or preferably an interferogram. Many preferred embodiments have an optical path difference of an interferometer or an interferogram is less than 2,000 μm, more preferably less than 1,000 μm, more preferably less than 750 μm, more preferably less than 500 μm, more preferably less than 300 μm, more preferably less than 200 μm, more preferably less than 100 μm, more preferably less than 75 μm, more preferably less than 50 μm, more preferably less than 30 μm, more preferably less than 20 μm, more preferably less than 10 μm.

Normally it is necessary to known the relationship between observed modulation of a signal and the corresponding optical path difference. According to the present invention many embodiments are based on that the acquisition of modulated signal is made with reference to external information or signal, preferably where reference information or signal reflects substantially position of a moving part of an interferometer, more preferably where reference signal is from a laser, for instance an He—Ne laser, more preferably where reference signal is from a laser diode, more preferably where reference signal is from a light emitting diode, e.g. a broad band source, at least when compared to a laser. In such embodiments, it is preferred that the number of acquired data points is equal to the number interference patterns of the reference signal (e.g. the wave properties of modulated He—Ne laser), preferably where the number of data points is 2 times the number of interference patterns or more, more preferably where the number of data points is 4 times the number of interference patterns or more, more preferably where the number of data points is 8 times the number of interference patterns or more, more preferably where the number of data points is 16 times the number of interference patterns or more, more preferably where the number of data points is 32 times the number of interference patterns or more, more preferably where the number of data points is 64 times the number of interference patterns or more. This allows for a more detailed structures of the interference signal to be revealed which is highly preferred in many embodiments.

On the other hand, many highly preferred embodiments of the current invention do not rely on an external source for such a reference signal. There it is preferred that the acquisition of modulated signal is made without reference to external information or signal, preferably where acquisition is made with reference to internal information or signal, e.g. identifiable features of the interference signals, more preferably with reference to time of movement of a moving part of an interferometer, simply relying on a reproducible movement of an optical component, and/or with reference to control signal to movement means moving a part of an interferometer, such as a digital information e.g. voltage, preferably where the reference to time or control signal is established or verified at predetermined intervals, preferably by the observation of properties of known material. For this purpose several embodiments employ one or more substances with known properties, e.g. a reference sample.

In these embodiments it is often preferred that the number of acquired data points is substantially equal to the expected number of interference patterns of a predetermined reference signal preferably modulated light, for instance for the purpose of allowing direct correlation to interference data obtained using such an external reference signal, preferably where the number of data points is 2 times the number of interference patterns or more, more preferably where the number of data points is 4 times the number of interference patterns or more, more preferably where the number of data points is 8 times the number of interference patterns or more, more preferably where the number of data points is 16 times the number of interference patterns or more, more preferably where the number of data points is 32 times the number of interference patterns or more, more preferably where the number of data points is 64 times the number of interference patterns or more, preferably where information about modulated signal is constructed by interpolation representing equal spacing of optical path difference.

In embodiments where the optical path difference is established through the movement of an optical component such as a mirror, preferably two mirrors, for instance a Michelson interferometer, many preferred embodiments of the current invention relate to a modulation means were both mirrors are moved during the scanning, preferably where the movement of the two mirrors results in increased maximum optical path difference, compared to the movement of only one of the mirrors.

An interferometer, preferred in many embodiments is Fabry-Perot interferometer, containing a partially reflecting mirror with reflectance of less than 1, preferably less than 0.9, more preferably less than 0.75, more preferably less than 0.5 more preferably less than 0.3, more preferably less than 0.2 more preferably less than 0.1. In other embodiments, in particular where requirements to spectral resolution are limited it is preferred to use a Fabry-Perot interferometer, containing two partially reflecting mirrors with reflectance of less than 1, preferably less than 0.9, more preferably less than 0.75, more preferably less than 0.5 more preferably less than 0.3, more preferably less than 0.2 more preferably less than 0.1.

Modulating means according to the present invention preferably employ "solid-state" actuators for the movement of an optical component, such as a mirror or a beam splitter of an interferometer, where "solid-state" refers to an electrical, magnetic or thermal motor preferably producing a substantially linear motion, preferably where the movement is brought about by a piezo-electric actuator, such as a solid piezo actuator or a diaphragm actuator, or the like.

In addition to the linear movement of optical components, rotation of such components can similarly be used to generate modulation of signals. One often preferred embodiment based on the rotation of optical components is the rotation of a beam splitter rotated about a point on the axis between the two mirrors, or when an interferometer is a Fabry-Perot interferometer, containing two or more reflecting surfaces which are substantially not moved relative to each other during analysis, but where the angular position of the reflecting surface relative to the sample or the source of signal is altered during analysis.

With regard to the detection of modulated light different embodiment make use of a detector sensitive to one or several of the following wavelength regions; ultra-violet light, visible light, near-infrared light, mid-infrared light, far infrared light. For that purpose, detectors such as of several of the following, silicium photo diode, photomultiplier tube, DTGS, MCT.

Many of the components used in the different embodiments of the current invention are affected by one or more environmental factors or properties, such as temperature, humidity or composition of the ambient air. Some of these environmental factors can be compensated for through the standardisation or calibration according to the current invention, while other embodiments use full or partial condition, for instance with respect to temperature, preferably where variations of temperature is limited, preferably where variations of temperature are less than ±5° C., more preferably where variations of temperature are less than ±2° C., more preferably where variations of temperature are less than ±1° C., more preferably where variations of temperature are less than ±0.5° C., more preferably where variations of temperature are less than ±0.1° C., preferably where the target temperature is higher than ambient temperature. Similarly with respect to humidity, preferably where the humidity is less than 10%, more preferably where the humidity is less than 1%, more preferably where the humidity is less than 0.1%, more preferably where the humidity is less than 0.01%, more preferably where the humidity is less than 0.001%, preferably where the humidity is conditioned through the user of humidity absorbent and/or by externally supplied dry gas, preferably nitrogen ($N_2$). Also with respect to carbon dioxide ($CO_2$) levels, preferably where the carbon dioxide level is less than 1%, more preferably where the humidity is less than 0.1%, more preferably where the humidity is less than 0.01%, more preferably where the humidity is less than 0.001%, more preferably where the humidity is less than 0.0001%, preferably where the carbon dioxide level is conditioned through the user of carbon dioxide absorbent and/or by externally supplied carbon dioxide free gas, preferably nitrogen ($N_2$). In other embodiments an interferometer is not conditioned with respect to physical and/or chemical properties, preferably where such property is one or several of the following: temperature, composition of air, humidity.

Much preferred embodiments use of a series of individual detectors arranged in an at least one dimensional array, preferably in a two dimensional array, preferably the arrangement of any modulating and/or focusing means allowing the information acquired by individual detectors to be correlated to a spatially defined part of a sample or specimen of a sample. Often it is preferred that at least two of the detectors reflect substantially different information about spectral property of the sample or specimen.

Often the preferred number of individual detectors in a row or a column is equal to or greater than 4, preferably greater than 8, more preferably greater than 16, more preferably greater than 32, more preferably greater than 64, more preferably greater than 128, more preferably greater than 256, more preferably greater than 512.

When the homogeneity of sample is limited it is often preferred that at least two detectors reflect substantially different spectral property of the sample or specimen, where such differences are caused by substantially different chemical composition or other properties of at least two parts of the sample or specimen, preferably where the combined information from two or more detectors can be used to create a spatial representation of variation in chemical composition or other properties of a sample or a specimen.

In the current context the term "interferogram" is referred to interference data, which is correlated to optical path difference, either through the assumption of equal distance between observations or when the optical path difference at a given observation is known. Generally an interferogram is a linear or non-linear combination of spectral components, while in some cases folded with properties such as self apodization. The common and often preferred interferogram, e.g. when considering an interferogram from a Michelson interferometer, contains information where substantially all spectral components show combined positive and/or negative effect (e.g. zero optical path difference or centre-burst in interferogram from a Michelson interferometer). Other interferograms, often equally preferred in several embodiments of the current invention contains no information where substantially all spectral components show combined positive and/or negative effect (e.g. zero optical path difference or centre-burst in interferogram from a Michelson interferometer).

One aspect relating to the information quality of the collected modulated light is the intensity resolution, e.g. in the digitalisation of an analogue signal (ADC). The result of the ADC is often obtained with a high resolution, such as a digital representation is 32 bits or less, more preferably where the representation is 24 bits or less, more preferably where the representation is 16 bits or less, more preferably where the representation is 12 bits or less, more preferably where the representation is 10 bits or less, more preferably where the representation is 8 bits or less. Often the low resolution of the ADC is compensated for, preferably where the amplification of the signal is varied during the measurement or where the signal is measured with two or more digitising means, each measuring signal with substantially different amplification, preferably where the information about modulated light is represented by taking into account the amplification.

Often it is preferred to transform collected modulated signals before its use for the assessment of a chemical or a physical property, preferably where the purpose of the transformation is to compensate for stationary and/or variable property of the modulation means and/or acquiring means, preferably where transformation is defined by one or several properties of acquired information, more preferably where transformation is defined by one or several properties of the acquired information being acquired. In particular, where the purpose of the transformation is to correlate information recorded at know times, to information concerning to optical path difference, preferably where the purpose is to derive information at known optical path difference, preferably at substantially equal distance of optical path difference.

Often preferred embodiments of the current invention are based on the collection of a single set of modulated signals (e.g. sweep), but preferably from 2 or more sweeps or scans, more preferably from 4 or more sweeps or scans, more preferably from 8 or more sweeps or scans, more preferably from 16 or more sweeps or scans, more preferably from 32 or more sweeps or scans, more preferably from 64 or more sweeps or scans, more preferably from 128 or more sweeps or scans, more preferably from 256 or more sweeps or scans, more preferably from 512 or more sweeps or scans, more preferably from 1,024 or more sweeps or scans, more preferably from 2,048 or more sweeps or scans, more preferably from 4,096 or more sweeps or scans, more preferably from 8,192 or more sweeps or scans, more preferably from 16,384 or more sweeps or scans. This allows the plurality of sweeps to be used to derive a variety of information concerning the measurement being conducted such as statistical properties, preferably where the statistical property is one or several of the following; arithmetic mean, weighted mean, geometric mean, harmonic mean, maximum, minimum, range, median, variance, standard deviation, any statistical moment, correlation to time or other reference, preferably where the statistical property is used to determine the property of a single scan, preferably where the statistical information is used to assess a chemical or a physical property of a sample. Preferably a factor, or collection of coherent properties (e.g. loadings), where factor information is one or several of the following: eigenvector, eigenvalue, principal component, principal component scores. These factor information can be used for diagnostics of individual sweeps, for the purpose of identifying "out of the ordinary" or outlier behaviour, or it can be used to include effects which vary from one sweep to the next, such as would be expected to be observed when measuring samples with low homogeneity.

Many preferred embodiments use the method include methods modifying modulated signal, preferably where information about modulated light is modified prior to correlation to chemical or physical property, preferably where the purpose of said modification is to facilitate or improve predictive performance of said correlation, preferably where said modification is done by one or more coefficients or transformations, preferably where said coefficients or transformations are determined on the bases of qualitative and/or quantitative properties of modulation mean and/or acquiring mean, more preferably where said coefficients or transformations are associated to individual modulation mean and/or acquiring mean, preferably where said modification has the effect of substantial quantitative and/or qualitative standardisation of acquired information. Further, preferably the acquired information has been transformed by a numerical function preferably where transformation is one or several of the following; addition, multiplication, polynomial, logarithmic, exponential, trigonometric. Preferably the purpose of the transformation is to make the relationship between acquired information and representation of chemical or physical property substantially linear.

Since the information about modulated signal or interferograms will generally not reflect infinitesimal modulation it is often preferred to apply a non-uniform-predetermined set of variables or a function (e.i. apodization) before correlated modulated signals or interferograms to the at least one property of a chemical component by the use of a calculation means, preferably where the apodization is determined on the bases of the property of the wave function information being generated, preferably where the purpose is to remove or suppress periodic or substantially periodic systematic effects. Often this apodization is different for different spectral elements or spectral features, preferably adapted to give enhanced output.

Various preferred embodiments of the current invention concern different spectroscopic applications, depending on the arrangement, such as were light is transmitted onto the sample or specimen, generally to determine the attenuation of light, and the modulated light is light which is transmitted through or onto the sample. Often this is preferably done by in addition taking into consideration a sample or specimen with known property (e.i. reference sample), more preferably where the known property is the substantial absence of the chemical or physical property (e.i. zero sample). Further other embodiments acquire or determine properties of reference sample substantially simultaneously with acquired information about sample or specimen (e.i. double beam spectroscopy), preferably where said information is not acquired or determined simultaneously with acquired information about sample or specimen (e.i. single beam spectroscopy), but where properties of a reference sample are stored from a previous measurement of a reference sample, or such properties are derived from the measurement of the sample.

The step of assessing chemical and/or physical properties preferably involves correlation to a set of coefficients, preferably where some or all of said coefficients are predetermined. The said set of coefficients is preferably a calibration model, preferably where said calibration model is derived from the measuring of one or several samples or specimens (e.i. calibration samples), preferably where one or more chemical or physical property of said samples or specimens is determined or known (e.i. reference values). Further the measuring of said calibration samples is performed under representative conditions which are substantially identical to conditions under which samples to be assessed are being measured, preferably where said conditions are environmental property (e.g. temperature, pressure), preferably where said conditions represent different instruments. Calibration models, generally preferred in the embodiments of the current invention are one or several of the following: Linear Regression (LR), Multiple Linear Regression (MLR), Principle Component model (PCA/PCR), Partial Least Squares (PLS), Artificial Neural Network (ANN) Multi Way calibration model.

An often preferred embodiment allows the construction of at lease partial spectral information. Preferably, by determining scores of a wave function, preferably where the wave function is a cosine or sine function of a single spectral element, more preferably where the wave function is a function representing a spectral feature, such as an attenuation or emission feature, preferably where the spectral feature comprises more than a single attenuation or emission feature, usually highly correlated.

The assessment according to the current invention can be applied to a variety of different samples representing one or more of the following: Aqueous sample, such as environmental sample, drinking water, bathing water, process water, cooling water; Biological sample, such as tissue sample, blood sample, urine sample, feces sample, cell culture sample, bacteria culture, yeast culture; Industrial sample such as oil sample, petroleum sample, grease sample, pharmaceutical sample; Food sample such as milk sample, dairy product sample, meat sample, fish sample, fruit sample, vegetable sample; Gaseous sample such as exhaust gas, fermentation gas, combustible gas. Generally the chemical and/or physical properties of these sample are one or more of the following: spectral property, temperature, turbidity, total organic material, dry material, dissolved material, chlorophyll, fibres, amino acids, proteins, fat, fatty acids, lipids, glyserids, cholesterol, enzymes, sugars, glucose, alcohols, ethanol, methanol, acids, citric acid, acidic acid, aliphats, aromats, ketones, aldebydes, pH, density, salinity, colour. Often the nature of the sample being analysed using embodiments of the current invention require sampling pre-treatment, such as grinding, milling, homogenising, dissolving, evaporating, heating, cooling, filtering, burning.

One highly preferred feature of the current invention is the sample is loaded into a sampling device prior to assessment, at least for the duration of acquiring of information about modulated light, said sampling device being one which is only in direct engagement with modulation means substantially for the duration of the acquiring of information about modulated light, preferably said sampling device being suited for the assessment of a single sample, preferably said sampling device being disposed of upon completion of assessment.

In general several preferred embodiments of the current invention are applicable to a wide variety of application, but preferred applications include process control, quality control, clinical diagnostics, environmental control.

EXAMPLE 1

A Michelson Interferometer

The Michelson interferometer is a device that can divide a beam of light (electromagnetic radiation) into two paths and then recombine the two beams. If the two beams travel exactly the same distance between they are recombined all spectral elements of the light are preserved. If on the other hand there is a different in the distance that the two beams have travelled then an interference of certain spectral elements occurs.

FIG. 1 illustrates a Michelson interferometer. A typical construction consists of two mirrors 101 and 102, a beamsplitter 103, light source 104 and detector 105. Light from the light source 106 reaches the beamsplitter where it is divided up into two beams, one which is reflected by the beamsplitter 107 and one which is transmitted through the beamsplitter 108. Both these beams are reflected from the respective mirrors and recombine on the beamsplitter and reflected on the detector (not illustrated in the figure).

Assuming that the light entering the interferometer consist of only one spectral element, and referring to the wave properties of light we get that when the two beams are recombined after travelling equal distance then the energy of the light is preserved. If the distance the two beams travel is changed, e.g. by moving one or both of the mirrors, the wave function of the two beams will be out of phase, to a certain degree, when they are recombined. When the difference in distance amounts to ½ of the wavelength they are completely out of phase and will therefore cancel each other out. When the distance amounts to 1/1 of the wavelength they are again in phase. As the difference increases then this phenomena repeats it self, thus being out of phase each time the difference amounts to a full number of wavelengths plus ½ wavelength and being in phase when the difference amounts to a full number of wavelengths. Thus an interference pattern appears on the detector as the difference in the light beam is changed.

When the light consists of a plurality of spectral elements each spectral element undergoes interference as described above. At one point, e.i. when the difference between the two mirrors (Optical Path Difference) is equal are all spectral elements in phase. At any other point the different spectral element have different phase relative to all other spectral elements.

The optical elements are preferably enclosed in, or attached to a physical construction 109 called "interferometer", where preferably the other components, such as light source, detector and mirror actuator (not shown) are also included. Finally all elements of the system, also including electrical components (not shown) are included in the instrument chassis 110. Preferably either or both of the interferometer or the chassis are conditioned with respect to environmental parameters, such as temperature or gas composition (means not shown).

Source of Light

The light is in principle any electromagnetic radiation. In practice the spectral region of the light is defined or limited by the spectral properties of the elements of the interferometer. In applications where the parameter of interest is attenuation or absorption of light by a sample, the sample has to be placed somewhere in the light path, such that the light reaching the detector has interacted with the sample. In many embodiments the sample is paced between the light source and the modulating means, while in others the sample is placed between the beam splitter and one of the mirrors, while in many preferred embodiments the sample is placed between the modulating means and the detector. The nature of the observed information depends on the position of the sample in relation to the different elements of the interferometer. In other applications, such as photoluminescence (fluorescence or phosphorescence), raman, scatter, reflectance or chemiluminescence the light being analysed stems directly or indirectly from the sample itself.

Detection

Normally the detector is a device sensitive to the light used in the application and thus directly measures the modulated light. In other applications the detector detects a secondary effect caused by the modulated light. This is for instance photo acoustic spectroscopy, where the modulated light generates acoustic signals in the sample and the detector is thus a microphone sensitive to the acoustic signals or pressure generated.

In order to synchronise data collection a reference light with known properties, generally lasers or laser diodes, is modulated and detected, normally with a separate detector. If the reference light is a laser with narrow waveband then its interference pattern will be a series of highs and lows. This information is then used to control the data collection.

EXAMPLE 2

A Michelson Interferometer According to the Present Invention

Figure 2:
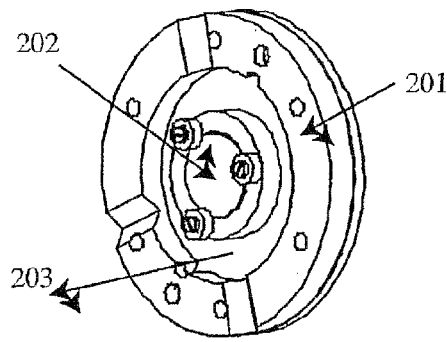
FIG. 2 illustrates a preferred construction of Michelson interferometer.
Figure 2:
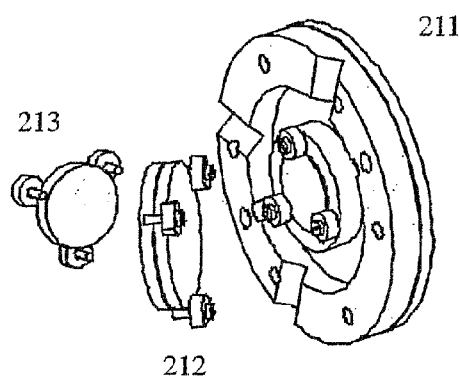
Figure 2:
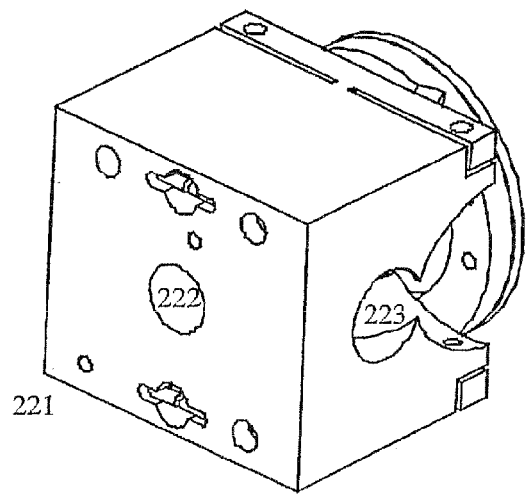

FIG. 2 illustrates a construction of a "solid" Michelson interferometer according to the present invention. The construction of a movable mirror is shown in FIG. 2A, where 201 is a frame on which a diaphragm piezo actuator 203 is attached (Piezomechanik Dr. Lutz Pickelmann GmbH, Germany). A mirror 202 is attached to the centre of the actuator.

The relative arrangement of the optical components of the interferometer is shown in FIG. 2B. The figure shows the movable mirror 211 and fixed mirror 213 and in between them a beam splitter 212.

Finally FIG. 2C shows a block of about 4×4×4 cm 221, in which the optical components are fixed. 222 illustrates the entrance of light (from a light source not shown) and 223 shows the exit of modulated light towards a detector (not shown). Further the block contains arrangement for the engagement of means for aligning of the mirrors (not shown).

The interferometer described above, can also be realised in an embodiment where the fixed mirror is replaced with a second, and preferably identical, movable mirror, thus accomplishing substantially double maximum optical path difference, when the two mirrors move substantially simultaneously, preferably but not necessary, at similar linear speeds.

EXAMPLE 3

A Fabry-Perot Interferometer According to the Present Invention

Figure 3:
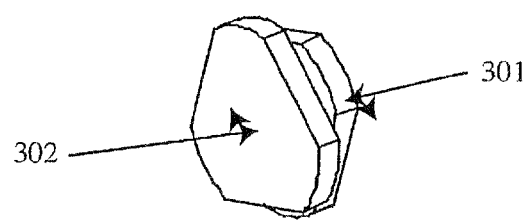
FIG. 3 illustrates a preferred construction of Fabry-Perot interferometer.
Figure 3:
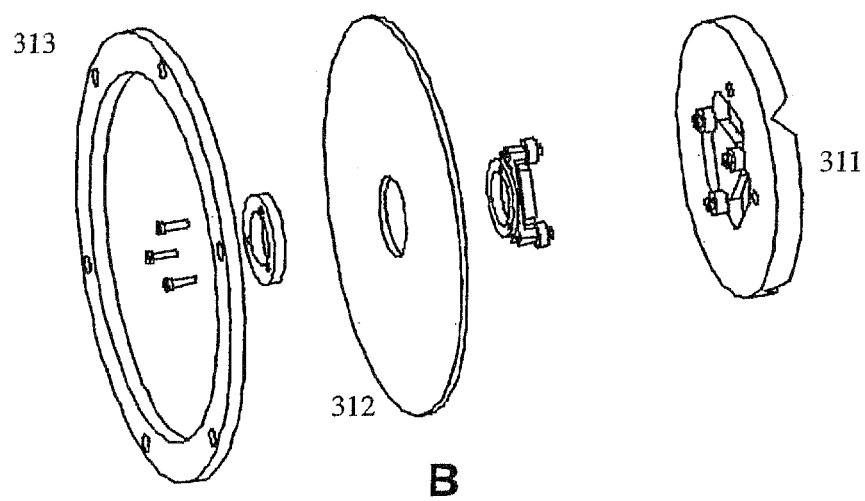
Figure 3:
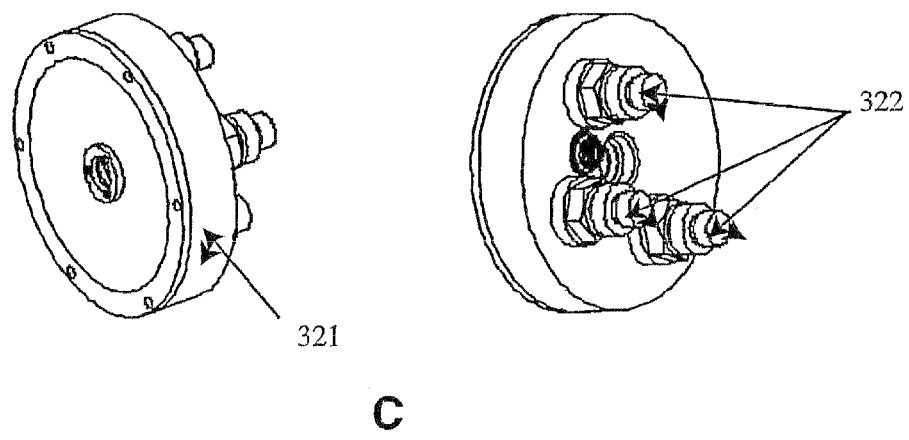

FIG. 3 illustrates a construction of a "solid" Fabry-Perot interferometer according to the present invention. The design an arrangement of the transparent mirror elements 301 and 302 is shown in FIG. 3A. The mirror elements are triangular in shape, and rotated 60 degrees relative to each other.

FIG. 3B shows a fixture 311, onto which one of the mirror elements is attached. Further a diaphragm piezo actuator 312 (Piezomechanik Dr. Lutz Pickelmann GmbH, Germany) is attached to the other mirror element. The actuator is attached to a rim 313.

FIG. 3C shows the casing of the interferometer, where 321 is a house, onto which the actuator and rim is attached. Further, three bolts 322 attach the fixture to the housing, allowing adjustment of the fixture, and thus mirror element 301 relative to the other actuator and thus the mirror element 302.

EXAMPLE 4

FT-IR Spectral Resolution

Figure 4:
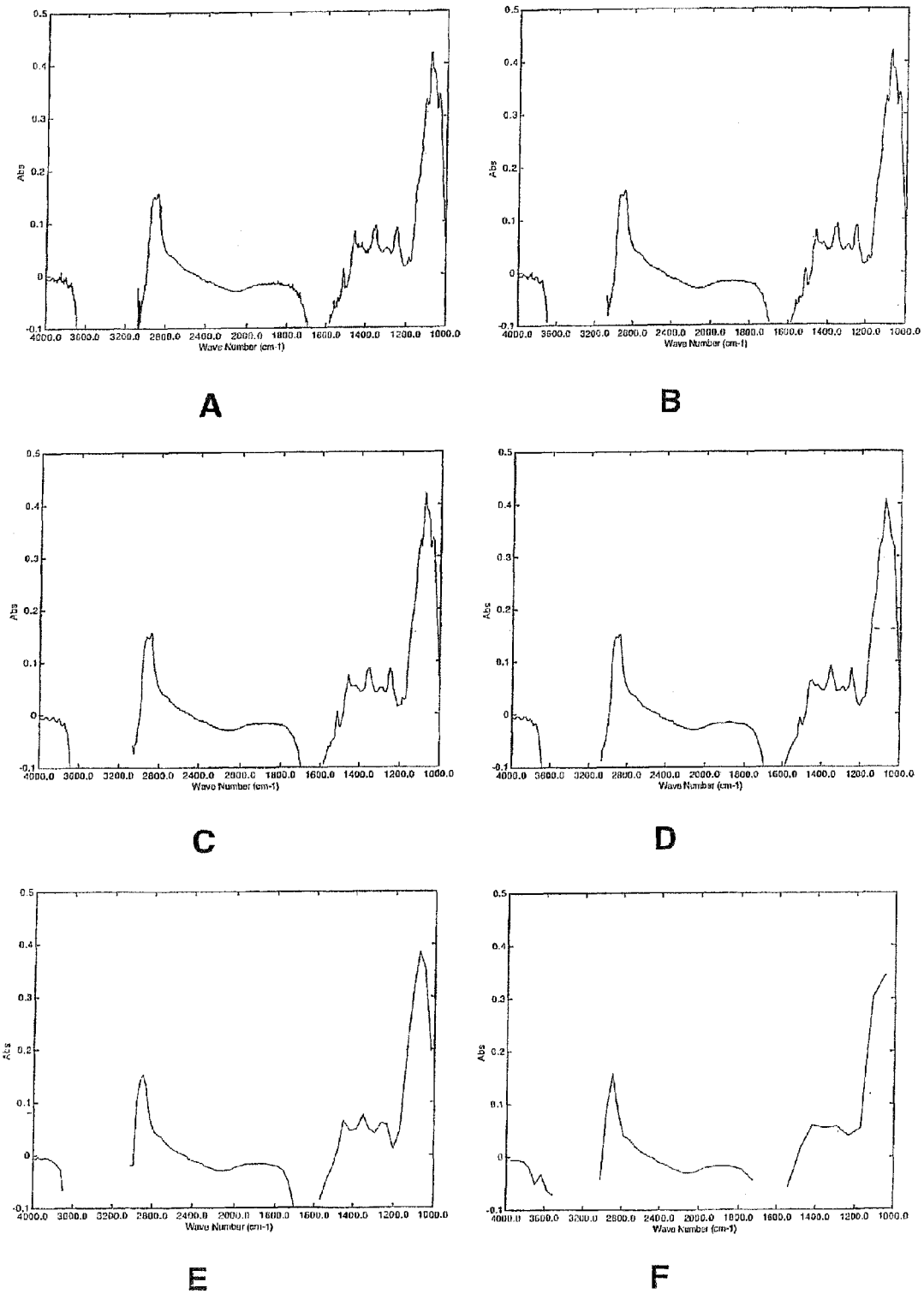
FIG. 4 illustrates effect of sweep length on resolution in FT-IR.

FIG. 4 shows FT-IR absorption spectrum of various spectral resolution of aqueous solution containing: Glucose 2.1%, Fructose 1.3%, Maltose 1.3%, Triton X-100 2.1% and PEG 1.1%. The spectrum was recorded on Bomem FT-IR spectrophotometer, 32 scans with nominal spectral resolution of 2 $cm^{-1}$ (8k interferogram). Figures A through F are calculated from the same interferograms (background and sample) without the use of any apodisation, were the length of the interferogram used in the Fourier Transformation is: A-8k resolution 2 $cm^{-1}$, B-4k resolution 4 $cm^{-1}$, C-2k resolution 8 $cm^{-1}$, D-1k resolution 16 $cm^{-1}$, E-½k resolution 32 $cm^{-1}$ and F-¼k resolution 64 $cm^{-1}$. The absorption of water in the regions around 1650 and 3400 $cm^{-1}$ is so strong, that the calculated absorption information is not reliable and these regions are therefore omitted from the spectra.

FIG. 4A shows a spectrum representing resolution of approximately 2 $cm^{-1}$, e.g. spectral data recorded for approximately every 1 $cm^{-1}$. This resolution is obtained from an 8k interferogram (8192 data points, or retardation of about 2.6 mm). The spectrum shows typical OH absorptions at about 1100 $cm^{-1}$ (width of main absorption band about 100 $cm^{-1}$, minor absorption band width about 10 $cm^{-1}$), CH absorptions in the region between 1200 and 1500 $cm^{-1}$ (width of absorption bands about 35 $cm^{-1}$) and CH3 at below 3000 cm⁻¹ (width about 100 cm⁻¹). In addition absorption of water gas are apparent as narrow absorptions in the regions around 1500, 1800 and around 3500 cm⁻¹. All these features are visible in the spectrum (peak width about 4 cm⁻¹).

FIG. 4B shows a spectrum representing resolution of approximately 4 cm⁻¹, e.g. spectral data recorded for approximately every 2 cm⁻¹. This resolution is obtained from a 4k interferogram (4096 data points, or Optical Path Difference, OPD, of about 2.6 mm). Compared to FIG. 4A, the main difference is the diminishing of the absorptions of water gas.

FIG. 4C shows a spectrum representing resolution of approximately 8 cm⁻¹, e.g. spectral data recorded for approximately every 4 cm⁻¹. This resolution is obtained from a 2k interferogram (2048 data points, or OPD of about 1.3 mm). Compared to FIGS. 4A and 4B, the main difference is the virtual elimination of the absorptions of water gas.

FIG. 4D shows a spectrum representing resolution of approximately 16 cm⁻¹, e.g. spectral data recorded for approximately every 8 cm⁻¹. This resolution is obtained from a 1k interferogram (1024 data points, or OPD of about 0.7 mm). Compared to FIGS. 4A, 4B and 4C, some of the fine features are lost, notably have the side peaks of the OH absorption transformed to shoulders.

FIG. 4E shows a spectrum representing resolution of approximately 32 cm⁻¹, e.g. spectral data recorded for approximately every 16 cm⁻¹. This resolution is Further the block contains arrangement for the engagement of means for aligning of the mirrors (not shown).

The interferometer described above, can also be realised in an embodiment where the fixed mirror is replaced with a second, and preferably identical, movable mirror, thus accomplishing substantially double maximum optical path difference, when the two mirrors move substantially simultaneously, preferably but not necessary, at similar linear speeds.

EXAMPLE 3

A Fabry-Perot Interferometer According to the Present Invention

FIG. 3 illustrates a construction of a "solid" Fabry-Perot interferometer according to the present invention. The design an arrangement of the transparent mirror elements 301 and 302 is shown in FIG. 3A. The mirror elements are triangular in shape, and rotated 60 degrees relative to each other.

FIG. 3B shows a fixture 311, onto which one of the mirror elements is attached. Further a diaphragm piezo actuator 312 (Piezomechanik Dr. Lutz Pickelmann GmbH, Germany) is attached to the other mirror element. The actuator is attached to a rim 313.

FIG. 3C shows the casing of the interferometer, where 321 is a house, onto which the actuator and rim is attached. Further, three bolts 322 attach the fixture to the housing, allowing adjustment of the fixture, and thus mirror element 301 relative to the other actuator and thus the mirror element 302.

EXAMPLE 4

FT-IR Spectral Resolution

FIG. 4 shows FT-IR absorption spectrum of various spectral resolution of aqueous solution containing: Glucose 2.1%, Fructose 1.3%, Maltose 1.3%, Triton X-100 2.1% and PEG 1.1%. The spectrum was recorded on Bomem FT-IR spectrophotometer, 32 scans with nominal spectral resolution of 2 cm⁻¹ (8k interferogram). Figures A through F are calculated from the same interferograms (background and sample) without the use of any apodisation, were the length of the interferogram used in the Fourier Transformation is: A-8k resolution 2 cm⁻¹, B-4k resolution 4 cm⁻¹, C-2k resolution 8 cm⁻¹, D-1k resolution 16 cm⁻¹, E-½k resolution 32 cm⁻¹ and F-¼k resolution 64 cm⁻¹. The absorption of water in the regions around 1650 and 3400 cm⁻¹ is so strong, that the calculated absorption information is not reliable and these regions are therefore omitted from the spectra.

FIG. 4A shows a spectrum representing resolution of approximately 2 cm⁻¹, e.g. spectral data recorded for approximately every 1 cm⁻¹. This resolution is obtained from an 8k interferogram (8192 data points, or retardation of about 2.6 mm). The spectrum shows typical OH absorptions at about 1100 cm⁻¹ (width of main absorption band about 100 cm⁻¹, minor absorption band width about 10 cm⁻¹), CH absorptions in the region between 1200 and 1500 cm⁻¹ (width of absorption bands about 35 cm⁻¹) and CH3 at below 3000 cm⁻¹ (width about 100 cm⁻¹). In addition absorption of water gas are apparent as narrow absorptions in the regions around 1500, 1800 and around 3500 cm⁻¹. All these features are visible in the spectrum (peak width about 4 cm⁻¹).

FIG. 4B shows a spectrum representing resolution of approximately 4 cm⁻¹, e.g. spectral data recorded for approximately every 2 cm⁻¹. This resolution is obtained from a 4k interferogram (4096 data points, or Optical Path Difference, OPD, of about 2.6 mm). Compared to FIG. 4A, the main difference is the diminishing of the absorptions of water gas.

FIG. 4C shows a spectrum representing resolution of approximately 8 cm⁻¹, e.g. spectral data recorded for approximately every 4 cm⁻¹. This resolution is obtained from a 2k interferogram (2048 data points, or OPD of about 1.3 mm). Compared to FIGS. 4A and 4B, the main difference is the virtual elimination of the absorptions of water gas.

FIG. 4D shows a spectrum representing resolution of approximately 16 cm⁻¹, e.g. spectral data recorded for approximately every 8 cm⁻¹. This resolution is obtained from a 1k interferogram (1024 data points, or OPD of about 0.7 mm). Compared to FIGS. 4A, 4B and 4C, some of the fine features are lost, notably have the side peaks of the OH absorption transformed to shoulders.

FIG. 4E shows a spectrum representing resolution of approximately 32 cm⁻¹, e.g. spectral data recorded for approximately every 16 cm⁻¹. This resolution is obtained from a ½k interferogram (512 data points, or OPD of about 0.3 mm). Compared to FIGS. 4A, 4B, 4C and 4D, most of the absorption features are now severely distorted.

FIG. 4F shows a spectrum representing resolution of approximately 64 cm⁻¹, e.g. spectral data recorded for approximately every 32 cm⁻¹. This resolution is obtained from a ¼k interferogram (256 data points, or OPD of about 0.15 mm). Compared to FIGS. 4A, 4B, 4C, 4D and 4E, only the main features are visible but severely distorted.

EXAMPLE 5

Simulation of Interferograms

Figure 5:
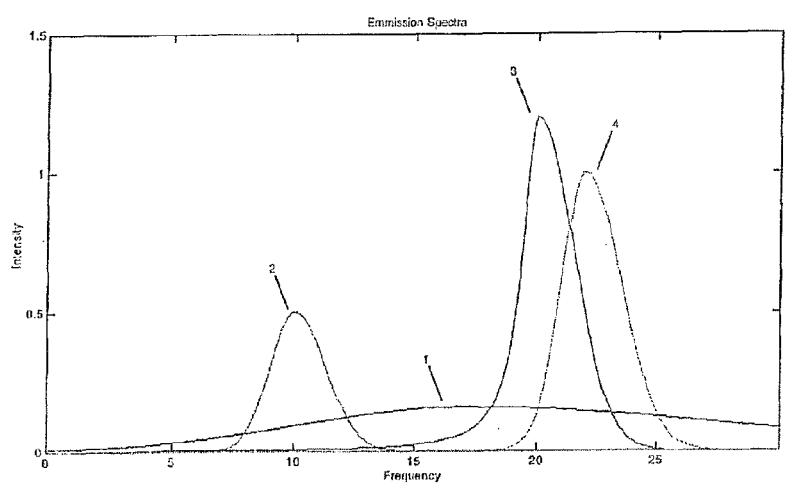
FIG. 5 illustrates a simulation of spectral data.
Figure 5:
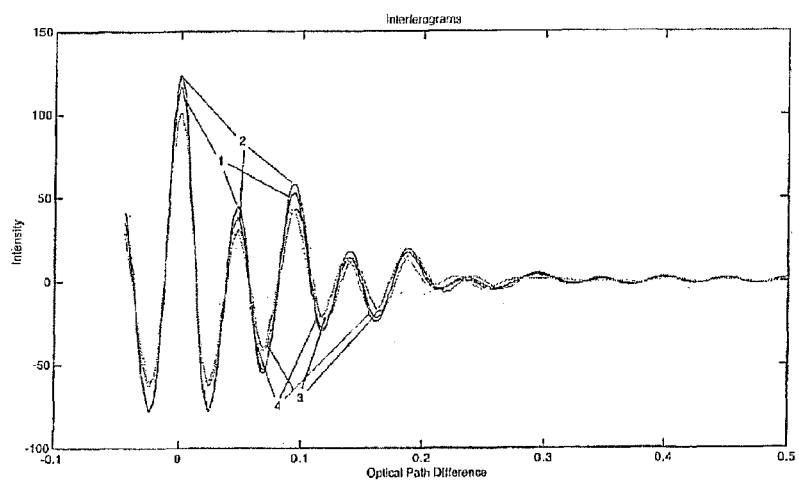
Figure 5:
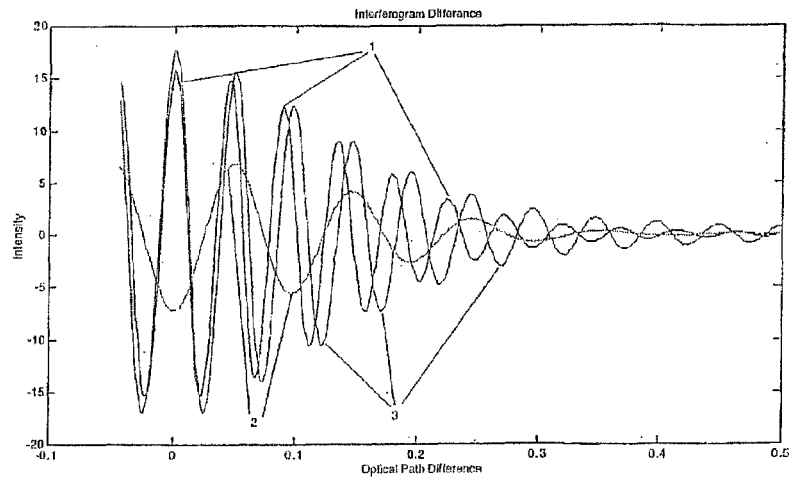

In order to illustrate properties of wave functions in interferograms a simulation of a simple system was used to construct interferogram. The simulated system concerns an emission system consisting of four emission sources representing different emission properties. FIG. 5A illustrates the emission sources, which are a broad "background" emission (line 1) and three "peaks", the first at frequency 10 (line 2), the second at frequency 20 (line 3) and the third at frequency 22 (line 4).

FIG. 5B illustrates three interferograms, calculated from the emission system (cosine wave functions), where the first interferogram (line 1) represents intensities as shown in FIG. 5A, the second interferogram (line 2) represent the emission system, where the intensity of the peak at frequency 22 is reduced, the third interferogram (line 3) represents the emission system, where the intensity of the peak at 10 is increased and the fourth interferogram (magenta) represents the emission system, where the intensity of the peak at 20 is reduced (line 4). In Fourier Transform Spectroscopy, the current system would need retardation of at least 1 in order to separate the peaks at frequencies 20 and 22.

The different interferogram illustrate the orthogonal nature of wave functions. The changes at different retardation in the second, third and fourth interferograms relative to the first interferogram are indeed not correlated, as is further illustrated in FIG. 5C, which shows the difference between the first interferogram and the second (line 1), third and first (line 2) and fourth and first (line 3).

The effect of changing the emission of the peak at frequency 10 (line 2 in FIG. 5C) is very obvious since the oscillations of this effect are slow compared to the other effects, which are located at frequencies 22 and 20. Further the differences between the effects of peaks 22 and 20 (lines 3 and 2 in FIG. 5C respectively) are pronounced, even at short retardation, e.g. at retardation 0.2 or even 0.1.

The findings of the simulation, illustrate that similar spectral features give rise to wave function combinations that are highly orthogonal, even at substantially small retardation compared to current methods. To a person skilled in the art of chemometric, it is obvious that properties of the system, such as absolute or relative intensities of the different emission sources can be obtained using interference data collected using limited retardation. Further it is evident, that regions of the interferogram not including the centerburst also show this property.

EXAMPLE 6

Spectral Information

Figure 6:
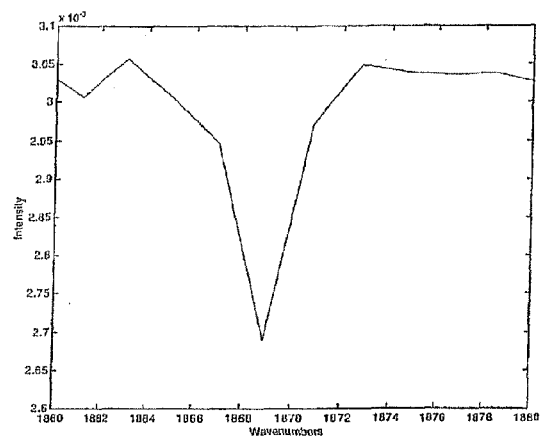
FIG. 6 illustrates the construction of spectral elements.
Figure 6:
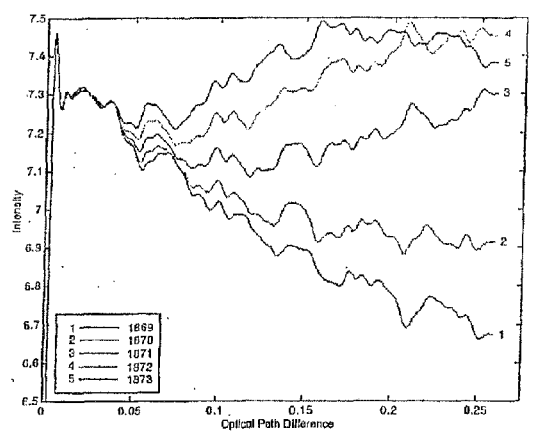
Figure 6:
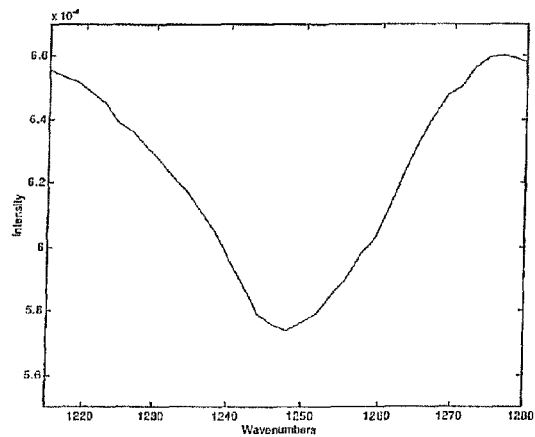
Figure 6:
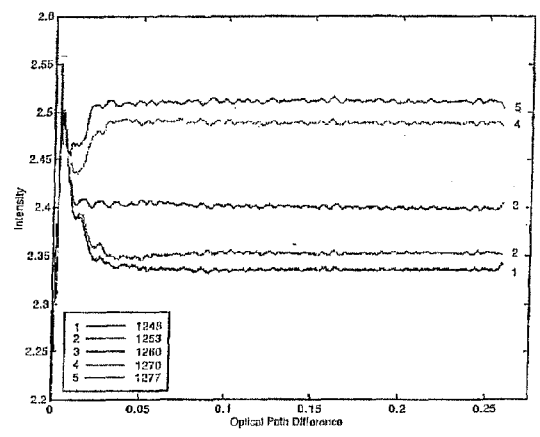

In order to illustrate the available information obtainable from an interferogram, a simulation was carried out using a single beam spectrum IR spectrum, collected using an 8k double sided interferogram. From this data, scores of cosine functions were extracted, at various Optical Path Differences (OPD). The results are illustrated in FIG. 6.

Firstly a narrow absorption band of water gas was investigated. The single beam intensity of the peak is illustrate in FIG. 6A. A number of frequencies representing the region from the peak top (1869 $cm^{-1}$) to the "base line" at 1873 $cm^{-1}$ were constructed from the region between centerburst and different OPD and the results are given in FIG. 6B. FIG. 6B illustrates a sharp rise in all frequencies shortly after the centerburst. Then in the region up to about 0.03 OPD all the frequencies coincide, but from OPD above 0.05 they are separated. The relative separation follows closely the expected pattern, although the amplitude of the different frequencies continues to evolve throughout the OPD investigated. This indicates that after OPD of about 0.03 the peak starts to take form, but that the construction of its "true" shape would require OPD of more than 0.25 (4k interferogram).

Secondly similar investigation was carried out on a wider peak at about 1250 $cm^{-1}$, shown in FIG. 6C, and the corresponding results are shown in FIG. 6D. FIG. 6D shows similar features as does FIG. 6B All the frequencies are formed shortly after the centerburst, and the peaks starts to be formed at OPD of about 0.01. The form of the peak is fairly stable after OPD of about 0.03, both with regard to intensities and shape.

The conclusion from the above is, that the form of the peak determines the necessary OPD to recreate its shape and intensity. On the other hand, at OPD shorter than this, can be used to obtain systematic information, both about the shape and the intensity of the peak. From the point of view of chemometrics (e.g. multivariate calibration), such information is often adequate for the purpose of performing an assessment of a chemical or physical property of a sample, by the use of an appropriate model since such a model can be based on properties correlating to the properties of the sample, while such properties only partly correlate to the spectroscopic properties of the sample.

EXAMPLE 7

Interferogram Standardisation

The interference of light upon modulation by e.g. a Michelson interferometer is inherently dependent on the spectral properties of the system used. The main factors are the property of the light source being modulated, optionally properties of a sample interacting with light from the light source, and finally properties of the optical components used, for instance mirrors, beamsplitter, detector. Among other things which can affect the observation of the interference, e.g. interferogram, is the position of the moving part forming the interference at the time of observation. A precise knowledge of the optical path difference (OPD) is a critical factor, which is normally obtained by modulating a monochromatic light using the same or similar optical system and using the simple waveform properties of this light to register or control the acquisition of the modulated signal.

Methods according to the present invention rely on other techniques for the determination of OPD. One preferred method is to use the inherent properties of the system at hand to obtain information about OPD and/or mirror movements. As mentioned above the properties of the system determine the result of the modulation. If for instance we consider the detection of transmitted energy, e.g. in the mid-ir region, then the output of the modulation is determined by the profile of the light source and the optical properties of the system. Thus the interferogram has certain properties which are purely dependent on the position of the modulating means. In the case where the precise position of the modulating means is not known, it is possible to locate one or more of the identifiable properties of the system and to use that information to, for instance, correlate time of observation, or other controlling parameter, to OPD. Depending on the properties of the system in use, this correlation to OPD can be reproducible for a longer or shorter time. Thus in some embodiments it is preferred to establish or verify this correlation for every scan performed by the interferometer, while in other equally preferred embodiments this is done at intervals, such as once per second, once per minute, once per hour, once per week or even longer. For many of the embodiments, it is preferred to introduce one or more means to the system, with known optical properties, to establish such identifiable properties. Apart from allowing the creation or verification of correlation to OPD, these methods further allow the determination of various other properties of the system, such as optical response.

Figure 7:
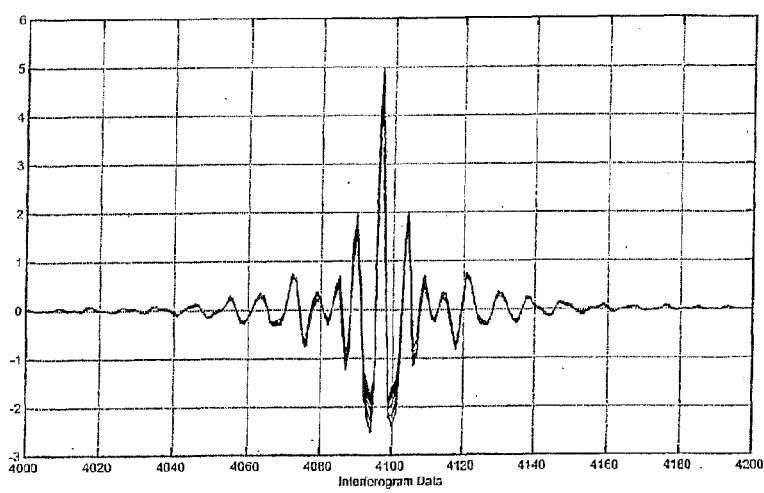
FIG. 7 illustrates properties of an interferogram.
Figure 7:
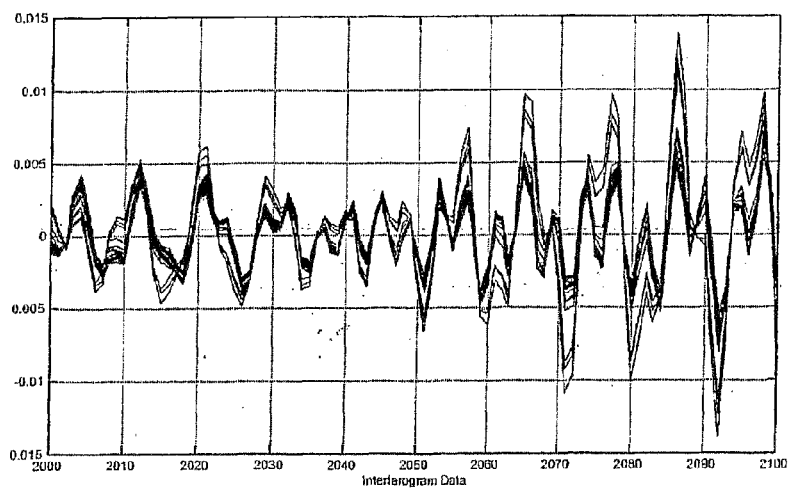
Figure 7:
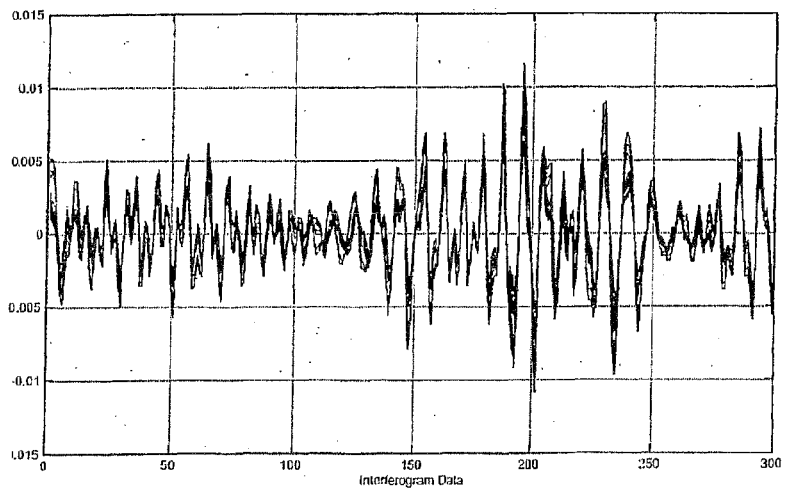

To illustrate some of the properties of modulation, FIGS. 7A through 7C show a number interferograms, collected on a Bomem FT-IR spectrophotometer (8k interferograms). The instrument uses a He—Ne laser to control the collection of data, to assure even an accurate determination of OPD. The figures show 73 individual interferograms (co added 64 scans) collected with an approximately 50 μm aqueous film in the light path, with between 0% and approximately 10% dissolved matter in various amounts (Lactose, Sucrose, Glucose, Fructose, Maltose, Triton X-100, PEG).

FIG. 7A illustrates the region around centerburst (zero ODP, data point 4097) for interferograms of all 73 individual samples. From the figure it is apparent that the centerburst region shows great likeness in all measurements, in particular concerning the position of highs and lows in the intensity.

Further FIG. 7B, which shows a region in the interferograms between data points 2000 and 2100 (OPD approximately −0.1 cm). This illustrates that the differences between the individual measurements is mainly seen in the intensities of the different highs and lows, while the position of the interferogram features is virtually identical.

FIG. 7C shows interferogram data at the beginning of the interferogram (OPD approximately −0.2 cm). As in FIGS. 7A and 7B the different measurement show some variation in intensity, but the position is virtually identical. Further, a relatively complex interference structure can be seen in the approximate region between data points 110 and 260. This illustrates that in addition to the individual highs and lows of the interferogram, such more complicated structures are reproduced in each of the measurement.

From the above it can be seen, that given a relatively stable optical system, that several features of the interferogram can be identified, and used for accurately determine the current OPD of the interferogram. To compensate for lack of stability in the optical system, it is possible to generate similar interferogram structures, using additional material, such as known absorbing/emitting material or interference filters. Such structure can subsequently be identified and used to characterise the modulation system, for instance to determine OPD.

The invention claimed is:

1. A method for the assessment of at least one chemical or physical property of a fluid or powder sample comprising;
    establishing modulation means, said modulation means comprising an interferometer, wherein an optical path difference in the range of 10 to 10,000 microns is obtained through the movement of at least one optical component in said interferometer using a solid-state actuator,
    interferometer modulating light emitted from the sample, having interacted with the sample and/or being emitted to the sample,
    detecting modulated light in the NIR and/or the IR spectral region or a property derived from said modulated light on at least one detector,
    correlating the obtained information to the at least one chemical or physical property, and wherein information about modulated light is an interferogram, and where the interferogram contains information from the zero optical path difference or centre-burst.

2. The method according to claim 1, wherein the light is modulated before being emitted to the sample.

3. The method according to claim 1, where the solid-state actuator is piezo electric actuator, thermal actuator or electrostatic actuator, such as a solid piezo actuator or a diaphragm actuator.

4. The method according to claim 1, wherein spectral resolution as defined by demodulated spectral information about light in the mid-IR region is less than 8 cm$^{-1}$, such as less than 16 cm$^{-1}$, less than 32 cm$^{-1}$, less than 64 cm$^{-1}$, less than 96 cm$^{-1}$, less than 128 cm$^{-1}$, less than 160 cm$^{-1}$, less than 192 cm$^{-1}$, less than 224 cm$^{-1}$, less than 256 cm$^{-1}$.

5. The method according to claim 1, wherein spectral resolution as defined by demodulated spectral information about light in the near-IR region is less than 8 cm$^{-1}$, such as less than 16 cm$^{-1}$, less than 32 cm$^{-1}$, less than 64 cm$^{-1}$, less than 96 cm$^{-1}$ less than 128 cm$^{-1}$, less than 160 cm$^{-1}$, less than 192 cm$^{-1}$, less than 224 cm$^{-1}$, less than 256 cm$^{-1}$.

6. The method according to claim 1, wherein the modulating means comprises at least one light source.

7. The method according to claim 6, wherein the light source emits light in the mid-IR region, near-IR region, visible region, UV region, where the light source is a thermal emitting light source, light emitting diode or laser diode, comprising one light source or more than one light source of similar or different properties.

8. The method according to claim 1, wherein light emitted onto, through or from a sample is of wavelength longer than 1,000 nm, such as longer than 1,500 nm, more preferably longer than 2,000 nm, more preferably longer than 2,500 nm.

9. The method according to claim 1, wherein light emitted onto, through or from a sample is of frequency between 10,000 and 800 cm$^{-1}$, such as between 5,000 and 900 cm$^{-1}$, more preferably between 3,000 and 1,000 cm$^{-1}$, more preferably between 2,000 and 1,000 cm$^{-1}$.

10. The method according to claim 1, wherein light emitted onto, through or from a sample is of frequency between 10,000 and 2,000 cm$^{-1}$, such as between 5,000 and 2,000 cm$^{-1}$, more preferably between 3,000 and 2,000 cm$^{-1}$.

11. The method according to claim 1, wherein spectral information is modulated in such a way that frequency or wavelength are substantially represented in time or distance domain, where the modulation is by the means of an interferometer, such as "Michelson Interferometer" or "Fabry-Perot Interferometer".

12. The method according to claim 1, wherein a sample is placed between a light source and the modulation means.

13. The method according to claim 1, wherein the modulation means is a "Michelson Interferometer" and where the sample is placed between the beam splitter and one of the mirrors.

14. The method according to claim 1, wherein collection angle of an interferometer is more than 5 degrees, such as more than 10 degrees, more than 15 degrees, more than 20 degrees, more than 30 degrees, more than 45 degrees.

15. The method according to claim 1, wherein the optical divergence of a modulation mean is more than 2 degrees, such as more than 4 degrees, more than 6 degrees, more than 8 degrees, more than 10 degrees, more than 15 degrees.

16. The method according to claim 1, wherein any of the physical dimensions of an interferometer are less than 30 cm, such as less than 20 cm, less than 15 cm, less than 10 cm, less than 8 cm, less than 6 cm, less than 4 cm, less than 3 cm, less than 2 cm, less than 1 cm.

17. The method according to claim 1, wherein the scan length of the at least one optical component in the interferometer is less than 1,000 μm, such as less than 750 μm, less than 500 μm, less than 300 μm, less than 200 μm, less than 100 μm, less than 75 μm, less than 50 μm, less than 30 μm, less than 20 μm, less than 10 μm.

18. The method according to claim 1, wherein the optical path difference of the interferometer is less than 2,000 μm, such as less than 1,000 μm, less than 750 μm, less than 500 μm, less than 300 μm, less than 200 μm, less than 100 μm, less than 75 μm, less than 50 μm, less than 30 μm, less than 20 μm, less than 10 μm.

19. The method according to claim 1, wherein the acquisition of modulated signal is made with reference to external information or signal, the reference information or signal reflecting substantially position of a moving part of an interferometer, the reference signal is from a laser, more preferably where reference signal is from a laser diode, more preferably where reference signal is from a light emitting diode.

20. The method according to claim 1, where acquisition of information about modulated signal is done with reference to a modulated reference signal with known properties, wherein the number of acquired data points is equal to the number interference patterns of the reference signal, where the number of data points is 2 times the number of interference patterns or more, such as where the number of data points is 4 times the number of interference patterns or more, where the number of data points is 8 times the number of interference patterns or more, where the number of data points is 16 times the number of interference patterns or more, where the number of data points is 32 times the number of interference patterns or more, where the number of data points is 64 times the number of interference patterns or more.

21. The method according to claim 1, wherein the acquisition of modulated signal is made without reference to external information or signal, or wherein the acquisition is made with reference to internal information or signal, or wherein the acquisition is made with reference to time of movement of the at least one optical component of the interferometer and/or with reference to the solid state actuator, where the reference to time is established or verified at predetermined intervals, by the observation of properties of known material.

22. The method according to claim 21, where acquisition of information about modulated signal is done without reference to a reference signal with known properties, wherein the number of acquired data points is substantially equal to the expected number of interference patterns of a predetermined reference signal preferably modulated light, where the number of data points is 2 times the number of interference patterns or more, such as where the number of data points is 4 times the number of interference patterns or more, where the number of data points is 8 times the number of interference patterns or more, where the number of data points is 16 times the number of interference patterns or more, where the number of data points is 32 times the number of interference patterns or more, where the number of data points is 64 times the number of interference patterns or more, where information about modulated signal is constructed by interpolation representing equal spacing of optical path difference.

23. The method according to claim 1, wherein the at least one optical component is a mirror.

24. The method according to claim 1, wherein the interferometer comprises at least two optical components, where two optical components are moved during the scanning, resulting in increased maximum optical path difference, compared to the movement of only one of the optical components.

25. The method according to claim 1, wherein the interferometer is a Fabry-Perot interferometer, containing at least one partially reflecting mirrors with reflectance of less than 1, such as less than 0.9, less than 0.75, less than 0.5 less than 0.3, less than 0.2, less than 0.1.

26. The method according to claim 1, wherein an interferometer is a Fabry-Perot interferometer, containing two or more reflecting surfaces which are substantially not moved relative to each other during analysis, but where the angular position of the reflecting surface relative to the sample or the source of signal is altered during analysis.

27. The method according to claim 1, wherein the modulated light is detected by a detector being one of the following, silicium photo diode, photomultiplier tube, DTGS, MCT.

28. The method according to claim 1, wherein a light path or a part of a light path, is conditioned with respect to temperature, where variations of temperature is limited, and are less than ±5° C., such as less than ±2° C., less than ±1° C., less than ±0.50 C, less than ±0.1° C., preferably where the target temperature is higher than ambient temperature.

29. The method according to claim 1, wherein the light path or a part of a light path, is conditioned with respect to humidity, where the humidity is less than 10%, where the humidity is less than 1%, where the humidity is less than 0.1%, where the humidity is less than 0.01%, where the humidity is less than 0.001%, and where the humidity is conditioned through the user of humidity absorbent and/or by externally supplied dry gas, preferably nitrogen ($N_2$).

30. The method according to claim 1, wherein a light path or a part of a light path, preferably an interferometer, is conditioned with respect to carbon dioxide ($CO_2$) levels, such as where the carbon dioxide level is less than 1%, where the humidity is less than 0.1%, where the humidity is less than 0.01%, where the humidity is less than 0.001%, where the humidity is less than 0.0001%, and where the carbon dioxide level is conditioned through the user of carbon dioxide absorbent and/or by externally supplied carbon dioxide free gas, preferably nitrogen ($N_2$).

31. The method according to claim 1, wherein a light path or a part of a light path, is not conditioned with respect to physical and/or chemical properties, where such property is one or several of the following: temperature, composition of air, humidity.

32. The method according to claim 1, wherein information about modulated light is acquired with the use of a series of individual detectors arranged in an at least one dimensional array, such as in a two dimensional array, and the arrangement of any modulating and/or focusing means allows the information acquired by individual detectors to be correlated to a spatially defined part of a sample or specimen of a sample.

33. The method according to claim 1, wherein substantially all the detectors provide substantially identical information about spectral property of the sample.

34. The method according to claim 1, wherein at least two of the detectors provide substantially different information about spectral property of the sample.

35. The method according to claim 33, wherein a the detectors are arranged in an array, where the number of individual detectors in a row or a column is equal to or greater than 4, such as greater than 8, greater than 16, greater than 32, greater than 64, greater than 128, greater than 256, greater than 512.

36. The method according to claim 32, wherein a at least two detectors provide substantially different spectral property of the sample or specimen, where such differences are caused by substantially different chemical composition or other properties of at least two parts of the sample or specimen, and where the combined information from two or more detectors can be used to create a spatial representation of variation in chemical composition or other properties of a sample or a specimen.

37. The method according to claim 1, wherein information about modulated light is an interferogram, and where the interferogram is a linear or non-linear combination of spectral components.

38. The method according to claim 1, wherein information about modulated light is an interferogram, and where the interferogram contains information where substantially all spectral components show combined positive and/or negative effect.

39. The method according to claim 1, wherein information about modulated light is an interferogram, and where the interferogram contains no information where substantially all spectral components show combined positive and/or negative effect.

40. The method according to claim 1, where the transformation results in correlation of information recorded at known times to information concerning to optical path difference, and where the purpose is to derive information at known optical path difference.

41. The method according to claim 40, wherein the information is derived at substantially equal distance of optical path difference.

42. The method according to claim 1, wherein the information about modulated light is modified to prior correlation to chemical of physical property.

43. The method according to claim 42, wherein:
said modification facilities or improves predictive performance of said correlation,
said modification is done by one or more coefficients or transformations,
said coefficients or transformations are determined on the basis of qualitative and/or quantitative properties of modulation mean and/or acquiring mean,
said coefficients or transformations are associated to individual modulation mean and/or acquiring mean, and
said modification has the effect of substantial quantitative and/or qualitative standardization of acquired information.

44. The method according to claim 1, wherein acquired information or transformed or modified acquired information being correlated to the at least one chemical and/or a physical property of a sample is from at least a single sweep or scan by modulating means, such as from 2 or more sweeps or scans, from 4 or more sweeps or scans, from 8 or more sweeps or scans, more preferably from 16 or more sweeps or scans, from 32 or more sweeps or scans, from 64 or more sweeps or scans, from 128 or more sweeps or scans, from 256 or more sweeps or scans, from 512 or more sweeps or scans, from 1,024 or more sweeps or scans, from 2,048 or more sweeps or scans, from 4,096 or more sweeps or scans, from 8,192 or more sweeps or scans, from 16,384 or more sweeps or scans.

45. The method according to claim 1, wherein information from 2 or more sweeps or scans is a statistical property of 2 or more sweeps or scans, and where the statistical property is one or several of the following; arithmetic mean, weighted mean, geometric mean, harmonic mean, maximum, minimum, range, median, variance, standard deviation, any statistical moment, correlation to time or other reference, the statistical property is used to determine the property of a single scan, and where the statistical information is used to assess a chemical or a physical property of a sample.

46. The method according to claim 45, wherein information from sweeps or scans is factor information, and where factor information is one or several of the following: eigenvector, eigenvalue, principal component, principal component scores.

47. The method according to claim 1, wherein the acquired information has been transformed by a numerical function preferably where transformation is one or several of the following; addition, multiplication, polynomial, logarithmic, exponential, trigonometric.

48. The method according to claim 1, wherein the acquired information has been weighted by non-uniform predetermined set of variables or a function including apodization, before being correlated to the at least one property of a chemical component by the use of a calculation means, where the apodization is determined on the basis of the property of the wave function information being generated, where the purpose is to remove or suppress periodic or substantially periodic systematic effects.

49. The method according to claim 1, wherein spectral information is determined by determining scores of a wave function, where the wave function is a cosine or sine function of a single spectral element, the wave function is a function representing a spectral feature, such as an attenuation or emission feature, preferably where the spectral feature comprises more than a single attenuation or emission feature.

50. The method according to claim 1, wherein the sample being assessed is a sample representing one of the following: aqueous sample, such as environmental sample, drinking water, bathing water, process water, cooling water; biological sample, such as tissue sample, blood sample, urine sample, feces sample, cell culture sample, bacteria culture, yeast culture; Industrial sample such as oil sample, petroleum sample, grease sample, pharmaceutical sample; food sample such as milk sample, dairy product sample, meat sample, fish sample, fruit sample, vegetable sample; gaseous sample such as exhaust gas, fermentation gas, combustible gas.

51. The method according to claim 1, wherein the chemical or physical property being assessed is one of the following: spectral property, temperature, turbidity, total organic material, dry material, dissolved material, chlorophyll, fibres, amino acids, proteins, fat, fatty acids, lipids, glyserids, cholesterol, enzymes, sugars, glucose, alcohols, ethanol, methanol, acids, citric acid, acidic acid, aliphats, aromats, ketones, aldehydes, pH, density, salinity, colour.

52. The method according to claim 1, wherein the sample being assessed has been subjected to prior processing, such as grinding, milling, homogenising, dissolving, evaporating, heating, cooling, filtering, burning.

53. The method according to claim 1, wherein the sample or a specimen of the sample being assessed is loaded into a sampling device prior to assessment, at least for the duration of acquiring of information about modulated light, said sampling device being one which is only in direct engagement with modulation means substantially for the duration of the acquiring of information about modulated light, said sampling device being suited for the assessment of a single sample and being disposed of upon completion of assessment.

54. A system for the assessment of at least one chemical or physical property of a fluid or powder sample comprising
modulation means, comprising an interferometer, wherein an optical path difference in the range of 10 to 10,000 microns is obtained through the movement of at least one optical component in said interferometer using a solid-state actuator, said interferometer being capable of modulating light emitted from the sample, having interacted with the sample and/or being emitted to the sample, at least one detector capable of detecting a light in the NIR and/or the IR spectral region or a property derived from said modulated light, means for correlating the obtained information to the at least one chemical or physical property and
wherein information about modulated light is an interferogram, and where the interferogram contains information from the zero optical path difference or centre-burst.

55. The system according to claim 54 wherein the sample is placed between the modulating means and the detector.

56. The system according to claim 54, wherein information about modulation light is modified prior to correlation to chemical or physical property.

57. The system according to claim 56, wherein:
the purpose of said modification is to facilitate or improve predictive performance of said correlation,
said modification is done by one or more coefficients or transformations,
said coefficients or transformations are determined on the basis of qualitative and/or quantitative properties of modulation mean and/or acquiring mean,
said coefficients or transformations are associated to individual modulation mean and/or acquiring mean,
said modification has the effect of substantial quantitative and/or qualitative standardization of acquired information.

58. The system according to claim 54, where the solid-state actuator is piezo electric actuator, thermal actuator or electrostatic actuator, such as a solid piezo actuator or a diaphragm actuator.

59. The system according to claim 54 wherein the modulating means comprises at least one light source.

60. The system according to claim 59 wherein the light source emits light in the mid-IR region, near-IR region, visible region, UV region, preferably where the light source is a thermal emitting light source, light emitting diode or laser diode, where the light source comprises one or more than one light source of similar or different properties.

61. The system according to claim 54, wherein light emitted onto, through or from a sample is of wavelength longer than 1,000 nm, such as longer than 1,500 nm, longer than 2,000 nm, longer than 2,500 nm.

62. The system according to claim 54, wherein light emitted onto, through or from a sample is of frequency between 10,000 and 800 $cm^{-1}$, such as between 5,000 and 900 $cm^{-1}$, between 3,000 and 1,000 $cm^{-1}$, between 2,000 and 1,000 $cm^{-1}$.

63. The system according to claim 61, wherein light emitted onto, through or from a sample is of frequency between 10,000 and 2,000 $cm^{-1}$, such as between 5,000 and 2,000 $cm^{-1}$, between 3,000 and 2,000 $cm^{-1}$.

64. The system according to claim 54, wherein spectral information is modulated in such a way that frequency or wavelength intensities are substantially represented in time or distance domain, where the modulation is by the means of an interferometer, such as "Michelson Interferometer" or "Fabry-Perot Interferometer".

65. The system according to claim 54, wherein a sample is placed between a light source and the modulation means.

66. The system according to claim 54, wherein the modulation means is a "Michelson Interferometer" and where the sample is placed between the beam splitter and one of the mirrors.

67. The system according to claim 54, wherein the collection angle of an interferometer is more than 5 degrees, such as more than 10 degrees, more than 15 degrees, than 20 degrees, than 30 degrees, than 45 degrees.

68. The system according to claim 54, wherein an optical divergence of a modulation mean is more than 2 degrees, such as more than 4 degrees, than 6 degrees, than 8 degrees, than 10 degrees, than 15 degrees.

69. The system according to claim 54, wherein any of the physical dimensions of an interferometer are less than 30 cm, such as less than 20 cm, less than 15 cm, less than 10 cm, less than 8 cm, less than 6 cm, less than 4 cm, less than 3 cm, less than 2 cm, less than 1 cm.

70. The system according to claim 54, wherein the scan length of the at least one optical component in the interferometer is less than 1,000 µM, such as less than 750 µm, less than 500 µm, less than 300 µm, less than 200 µm, less than 100 µm, less than 75 µm, less than 50 µm, less than 30 µm, less than 20 µm, less than 10 µm.

71. The system according to claim 54, wherein the optical path difference of the interferometer is less than 2,000 µm, such as less than 1,000 µm, less than 750 µm, less than 500 µm, less than 300 µm, less than 200 µm, less than 100 µm, less than 75 µm, less than 50 µm, less than 30 µm, less than 20 µm, less than 10 µm.

72. The system according to claim 54, wherein the acquisition of modulated signal is made with reference to external information or signal, the reference information or signal reflects substantially position of a moving part of an interferometer, where reference signal is from a light emitting diode, laser or laser diode.

73. The system according to claim 54, where acquisition of information about modulated signal is done with reference to a modulated reference signal with known properties, wherein the number of acquired data points is equal to the number interference patterns of the reference signal, the number of data points is 2 times the number of interference patterns or more, such as where the number of data points is 4 times the number of interference patterns or more, the number of data points is 8 times the number of interference patterns or more, the number of data points is 16 times the number of interference patterns or more, the number of data points is 32 times the number of interference patterns or more, the number of data points is 64 times the number of interference patterns or more.

74. The system according to claim 54, wherein the acquisition of modulated signal is made without reference to external information or signal, wherein acquisition is made with reference to internal information or signal, or wherein the acquisition is made with reference to time of movement of the at least one optical component of the interferometer and/or with reference to the solid state actuator, where the reference to time is established or verified at predetermined intervals, by the observation of properties of known material.

75. The system according to claim 74, where acquisition of information about modulated signal is done without reference to a reference signal with known properties, wherein the number of acquired data points is substantially equal to the expected number of interference patterns of a predetermined reference signal preferably modulated light, the number of data points is 2 times the number of interference patterns or more, such as where the number of data points is 4 times the number of interference patterns or more, where the number of data points is 8 times the number of interference patterns or more, where the number of data points is 16 times the number of interference patterns or more, where the number of data points is 32 times the number of interference patterns or more, where the number of data points is 64 times the number of interference patterns or more, information about modulated signal is constructed by interpolation representing equal spacing of optical path difference.

76. The system according to claim 54, wherein the at least one optical component is a mirror.

77. The system according to claim 54, wherein the interferometer comprises at least two optical components, where two optical components are moved during the scanning, the movement of the two optical components results in increased maximum optical path difference, compared to the movement of only one of the optical components.

78. The system according to claim 54, wherein the interferometer is a Fabry-Perot interferometer, containing at least one partially reflecting mirrors with reflectance of less than 1, such as less than 0.9, less than 0.75, less than 0.5 less than 0.3, less than 0.2, less than 0.1.

79. The system according to claim 54, wherein an interferometer is a Fabry-Perot interferometer, containing two or more reflecting surfaces which are substantially not moved relative to each other during analysis, but where the angular position of the reflecting surface relative to the sample or the source of signal is altered during analysis.

80. The system according to claim 54, wherein the modulated light is detected by a detector being one of the following, silicium photo diode, photomultiplier tube, DTGS, MCT.

81. The system according to claim 54, wherein the light path or a part of a light path, is conditioned with respect to temperature, where variations of temperature is limited, such as where variations of temperature are less than ±5° C., where variations of temperature are less than ±2° C., where variations of temperature are less than ±1° C., where variations of temperature are less than ±0.5° C., where variations of temperature are less than ±0.10 C, preferably where the target temperature is higher than ambient temperature.

82. The system according to claim 54, wherein the light path or a part of a light path, is conditioned with respect to humidity, where the humidity is less than 10%, such as where the humidity is less than 1%, where the humidity is less than 0.1%, where the humidity is less than 0.01%, where the humidity is less than 0.001%, the humidity is conditioned through the user of humidity absorbent and/or by externally supplied dry gas, preferably nitrogen ($N_2$).

83. The system according to claim 54, wherein the light path or a part of a light path, is conditioned with respect to carbon dioxide ($CO_2$) levels, where the carbon dioxide level is less than 1%, preferably where the carbon dioxide level is conditioned through the user of carbon dioxide absorbent and/or by externally supplied carbon dioxide free gas, preferably nitrogen ($N_2$).

84. The system according to claim 54, wherein a light path or a part of a light path, is not conditioned with respect to physical and/or chemical properties, where such property is one or several of the following: temperature, composition of air, humidity.

85. The system according to claim 54, wherein information about modulated light is acquired with the use of a series of individual detectors arranged in an at least one dimensional array, such as in a two dimensional array, preferably the arrangement of any modulating and/or focusing means allows the information acquired by individual detectors to be correlated to a spatially defined part of a sample or specimen of a sample.

86. The system according to the claim 54, wherein substantially all the detectors provide substantially identical information about spectral property of the sample.

87. The system according to claim 54, wherein at least two of the detectors provide substantially different information about spectral property of the sample.

88. The system according to claim 86, wherein a the detectors are arranged in an array, where the number of individual detectors in a row or a column is equal to or greater than 4, such as greater than 8, greater than 16, greater than 32, greater than 64, greater than 128, greater than 256, greater than 512.

89. The system according to claim 85, wherein a at least two detectors provide substantially different spectral property of the sample or specimen, where such differences are caused by substantially different chemical composition or other properties of at least two parts of the sample or specimen, where the combined information from two or more detectors can be used to create a spatial representation of variation in chemical composition or other properties of a sample or a specimen.

90. The system according to claim 54, wherein information about modulated light is an interferogram, where the interferogram is a linear or non-linear combination of spectral components.

91. The system according to claim 54, wherein information about modulated light is an interferogram, where the interferogram contains information where substantially all spectral components show combined positive and/or negative effect.

92. The system according to claim 54, wherein information about modulated light is an interferogram, where the interferogram contains no information where substantially all spectral components show combined positive and/or negative effect.

93. The system according to claim 54, where the purpose of the transformation is to correlate information recorded at known times, to information concerning to optical path difference, where the purpose is to derive information at known optical path difference.

94. The system according to claim 93, wherein the information is derived substantially equal distance of optical path difference.

95. The system according to claim 54, wherein acquired information or transformed or modified acquired information being correlated to the at least one chemical and/or a physical property of a sample is from a single sweep or scan by modulating means, such as from 2 or more sweeps or scans, from 4 or more sweeps or scans, from 8 or more sweeps or scans, from 16 or more sweeps or scans, from 32 or more sweeps or scans, from 64 or more sweeps or scans, from 128 or more sweeps or scans, from 256 or more sweeps or scans, from 512 or more sweeps or scans, from 1,024 or more sweeps or scans, from 2,048 or more sweeps or scans, from 4,096 or more sweeps or scans, from 8,192 or more sweeps or scans, from 16,384 or more sweeps or scans.

96. The system according to claim 54, wherein information from 2 or more sweeps or scans is a statistical property of 2 or more sweeps or scans, where the statistical property is one or several of the following; arithmetic mean, weighted mean, geometric mean, harmonic mean, maximum, minimum, range, median, variance, standard deviation, any statistical moment, correlation to time or other reference, where the statistical property is used to determine the property of a single scan, and the statistical information is used to assess a chemical or a physical property of a sample.

97. The system according to claim 96, wherein information from sweeps or scans is factor information, preferably where factor information is one or several of the following: eigenvector, eigenvalue, principal component, principal component scores.

98. The system according to claim 54, wherein the acquired information has been transformed by a numerical function preferably where transformation is one or several of the following; addition, multiplication, polynomial, logarithmic, exponential, trigonometric.

99. The system according to claim 54, wherein the acquired information has been weighted by non-uniform predetermined set of variables or a function including apodization, before being correlated to the at least one property of a chemical component by the use of a calculation means, where the apodization is determined on the bases of the property of the wave function information being generated, where the purpose is to remove or suppress periodic or substantially periodic systematic effects.

100. The system according to claim 1, wherein spectral information is determined by determining scores of a wave function, where the wave function is a cosine or sine function of a single spectral element, where the wave function is a function representing a spectral feature, the spectral feature comprises more than a single attenuation or emission feature.

101. The system according to claim 1, wherein the sample or a specimen of the sample being assessed is loaded into a sampling device prior to assessment, at least for the duration of acquiring of information about modulated light, said sampling device being one which is only in direct engagement with modulation means substantially for the duration of the acquiring of information about modulated light, said sampling device being suited for the assessment of a single sample, and is being disposed of upon completion of assessment.

102. A method for the assessment of at least one chemical or physical property of a fluid or powder sample comprising
  establishing modulation means, said modulation means comprising an interferometer, wherein an optical path difference in the range of 10 to 10000 microns is obtained through the movement of at least one optical component in said interferometer using a solid-state actuator,
  interferometer modulating light emitted from the sample, having interacted with the sample and/or being emitted to the sample,
  detecting modulated light or a property derived from said modulated light on at least one detector, wherein acquisition of information about the modulated light signal is made without reference to external information or external signal,
  correlating information about the detected light to an optical path length obtaining an interferogram, and
  correlating the obtained interferogram, and/or the information about the detected light and the optical path length to the at least one chemical or physical property where the interferogram contains information from the zero optical path difference centre-burst.

103. A system for the assessment of at least one chemical or physical property of a fluid or powder sample comprising a modulation means, said modulation means comprising an interferometer, wherein an optical path difference is obtained in the range of 10 to 10000 microns through the movement of at least one optical component in said interferometer using a solid-state actuator, said interferometer being capable of modulating light emitted from the sample, having interacted with the sample and/or being emitted to the sample,
  at least one detector capable of detecting modulated light or a property derived from said modulated light, wherein acquisition of information about the modulated light signal is made without reference to external information or external signal,
  a means for correlating information about the detected light to an optical path length obtaining an interferogram, and
  a means for correlating the obtained interferogram, and/or the information about the detected light and the optical path length to the at least one chemical or physical property where the interferogram contains information from the zero optical path different difference or centre-burst.

104. A method for the assessment of at least one chemical or physical property of a fluid or powder sample comprising a) obtaining an interferogram representing detected modulation of light having interacted with the sample, where the information in the interferogram can be correlated to optical path difference which is in the range of 10 to 10000 microns, obtained through the movement of at least one optical component in said interferometer using a solid-state actuator, where the interferogram contains from the zero optical path difference or centre-burst,
b) determining or estimating interference loadings for a single spectral element or a single spectral feature corresponding to the said correlation to optical path difference and under conditions substantially similar to conditions forming the interferogram,
c) optionally repeating step b) a predetermined number of times,
d) determining scores of interference loadings in said interferogram, and
e) correlating said scores to the at least one chemical or physical property.

105. The method according to claim 104, wherein the scores determined in step d) is transformed to a spectrum.

106. A system for the assessment of at least one chemical or physical property of a fluid or powder sample comprising
  a) means for obtaining an interferogram representing detected modulation of light having interacted with the sample, where the information in the interferogram can be correlated to optical path difference which is in the range of 10 to 10000 microns, obtained through the movement of at least one optical component in said interferometer using a solid-state actuator, where the interferogram contains from the zero optical path difference or centre-burst,
  b) at least one detector for determining or estimating interference loadings for a single spectral element or a single spectral feature corresponding to the said correlation to optical path difference and under conditions substantially similar to conditions forming the interferogram,
  c) means for optionally repeating step b) a predetermined number of times,
  d) means for determining scores of interference loadings in said interferogram, and
  e) means for correlating said scores to the at least one chemical or physical property.

107. The system according to claim 106, comprising means for transforming the scores determined to a spectrum.

108. A method for standardizing an interferometer for the assessment of at least one chemical or physical property of a fluid or powder sample according to claim 1, said method comprising
  a. generating at least one interferogram from at least one standardization sample in said interferometer,
  b. providing a standard interferogram for said standard sample or for at least one standard feature,
  c. correlating said standard interferogram to said at least one interferogram obtained in step a), and
  d. standardizing the interferometer based on correlation information obtained in step c).

109. The method according to claim 108, wherein the correlation in step c) is conducted by correlating time of observation to optical path difference.

110. The method according to claim 108, wherein the correlation is performed for every scan performed by the interferometer.

111. The method according to claim 108, wherein the correlation is performed at predetermined frequency or time intervals.

112. The method according to claim 108, wherein the standard sample is selected from one of the following: aqueous sample, such as environmental sample, drinking water, bathing water, process water, cooling water; biological sample, such as tissue sample, blood sample, urine sample, feces sample, cell culture sample, bacteria culture, yeast culture; Industrial sample such as oil sample, petroleum sample, grease sample, pharmaceutical sample; food sample such as milk sample, dairy product sample, meat sample, fish sample, fruit sample, vegetable sample; gaseous sample such as exhaust gas, fermentation gas, combustible gas.

113. The method according to claim 108, wherein the interferogram of a standard feature is the interferogram of water.

114. A method for the assessment of at least one chemical or physical property of a fluid or powder sample comprising establishing an interferometer standardized as defined in claim 108, obtaining at least one interferogram from the sample, standardizing the interferogram based on standardisation parameters obtained from standardization of the interferometer, and correlating the standardized interferogram or information derived from said interferogram to the at least one chemical or physical property of the sample.

115. A system for the assessment of at least one chemical or physical property of a fluid or powder sample comprising an interferometer standardized as defined in claim 108, a means for obtaining at least one interferogram from the sample, a means for standardizing the interferogram based on standardisation parameters obtained from standardization of the interferometer, and a means for correlating the standardized interferogram or information derived from said interferogram to the at least one chemical or physical property of the sample.

116. The method according to claim 1, wherein the Game sample is placed between the modulating means and the detector.

* * * * *